(12) United States Patent
Yamada et al.

(10) Patent No.: US 11,124,881 B2
(45) Date of Patent: Sep. 21, 2021

(54) HYDROPHILIC METAL SURFACE TREATMENT AGENT

(71) Applicants: CHEMICAL DENSHI CO., LTD., Kanagawa (JP); Tokushima University, Tokushima (JP)

(72) Inventors: Shoichi Yamada, Kanagawa (JP); Toshio Hyuga, Kanagawa (JP); Hisao Nemoto, Tokushima (JP)

(73) Assignees: CHEMICAL DENSHI CO., LTD., Kanagawa (JP); TOKUSHIMA UNIVERSITY, Tokushima (JP)

( * ) Notice: Subject to any disclaimer, the term of this patent is extended or adjusted under 35 U.S.C. 154(b) by 0 days.

(21) Appl. No.: 17/272,765

(22) PCT Filed: Jun. 4, 2020

(86) PCT No.: PCT/JP2020/022193
§ 371 (c)(1),
(2) Date: Mar. 2, 2021

(87) PCT Pub. No.: WO2020/255741
PCT Pub. Date: Dec. 24, 2020

(65) Prior Publication Data
US 2021/0246560 A1   Aug. 12, 2021

(30) Foreign Application Priority Data

Jun. 17, 2019   (JP) .............................. JP2019-112183

(51) Int. Cl.
| | |
|---|---|
| C23F 11/12 | (2006.01) |
| C07D 319/06 | (2006.01) |
| C23F 11/16 | (2006.01) |
| C07C 327/22 | (2006.01) |
| C07D 317/20 | (2006.01) |

(52) U.S. Cl.
CPC ............ *C23F 11/12* (2013.01); *C07C 327/22* (2013.01); *C07D 317/20* (2013.01); *C07D 319/06* (2013.01); *C23F 11/16* (2013.01)

(58) Field of Classification Search
None
See application file for complete search history.

(56) References Cited

U.S. PATENT DOCUMENTS

| | | |
|---|---|---|
| 2005/0208015 A1 | 9/2005 | Nemoto et al. |
| 2015/0152565 A1 | 6/2015 | Yomogida |

FOREIGN PATENT DOCUMENTS

| | | |
|---|---|---|
| JP | 2001-152363 | 6/2001 |
| JP | 2003-129257 | 5/2003 |
| JP | 2010-99817 | 5/2010 |
| JP | 2011-178698 | 9/2011 |
| JP | 2015-105417 | 6/2015 |
| JP | 2015-172214 | 10/2015 |
| WO | 2004/029018 | 4/2004 |
| WO | 2008/093655 | 8/2008 |
| WO | 2013/035899 | 3/2013 |
| WO | 2018/131709 | 7/2018 |

OTHER PUBLICATIONS

International Search Report dated Sep. 8, 2020 in International (PCT) Application No. PCT/JP2020/022193.
Written Opinion of the International Searching Authority dated Sep. 8, 2020 in International (PCT) Application No. PCT/JP2020/022193, with English translation.
Hattori et al., "An Efficient Method for the Refinement of 1,3-Methyleneglycerol via Bridged Acetal Exchange and the Synthesis of a Symmetrically Branched Glycerol Trimer", Synthesis, 2012, vol. 44, pp. 2365-2373.
Nemoto et al., "Synthesis and evaluation of water-soluble resveratrol and piceatannol via BGLation", Bioorganic & Medicinal Chemistry Letters, vol. 22, Issue 15, Aug. 1, 2012, pp. 5051-5054.
Bandyopadhyay et al., "Anti-Fouling Chemistry of Chiral Monolayers: Enhancing Biofilm Resistance on Racemic Surface", Langmuir, vol. 27, No. 10, May 17, 2011, pp. 6124-6131.
Office Action dated May 8, 2021 in corresponding Chinese Patent Application No. 202080004543.4, with English Translation.

*Primary Examiner* — Joseph R Kosack
(74) *Attorney, Agent, or Firm* — Wenderoth, Lind & Ponack, L.L.P.

(57) ABSTRACT

The objective of the present invention is to provide a hydrophilic metal surface treatment agent by which a water-repellent property can be given to a metal surface with suppressing a corrosion and a discolorment of the metal, a method for treating a surface of a metal by using the hydrophilic metal surface treatment agent, a synthetic intermediate compound of a branched glycerol derivative as an active ingredient of the hydrophilic metal surface treatment agent, and a method for efficiently producing the synthetic intermediate compound. The hydrophilic metal surface treatment agent of the present invention is characterized in comprising the branched glycerol derivative represented by the following formula (I) as an active ingredient.

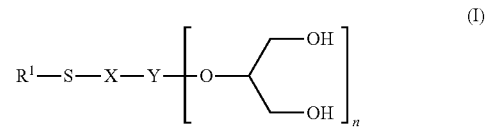

wherein $R^1$ is a hydrocarbon group having a carbon number of 10 or more and 30 or less, X is S or a carbonyl group, Y is an n+1 valent linker group, n is an integer of 1 or more and 5 or less.

12 Claims, 4 Drawing Sheets

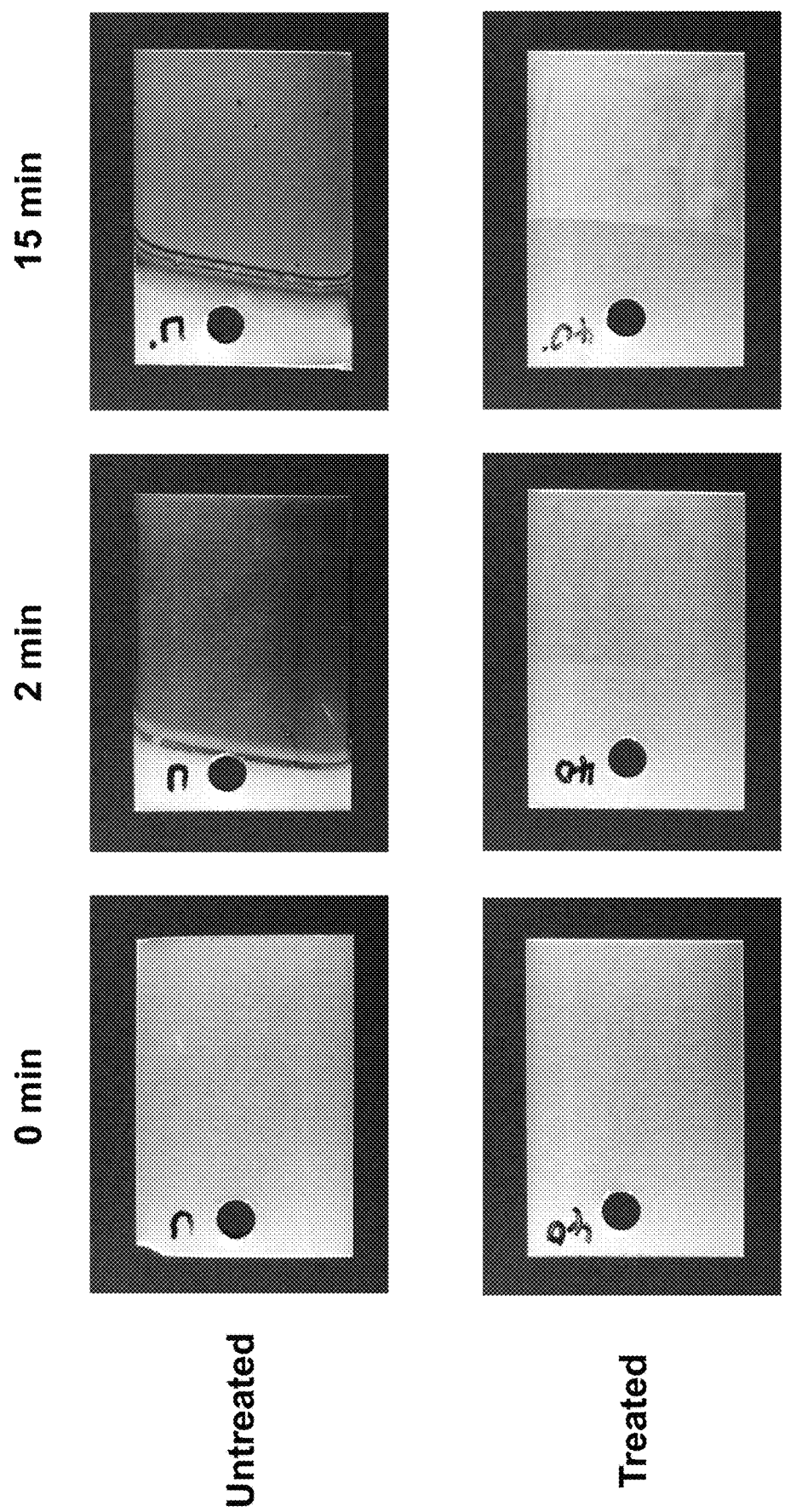

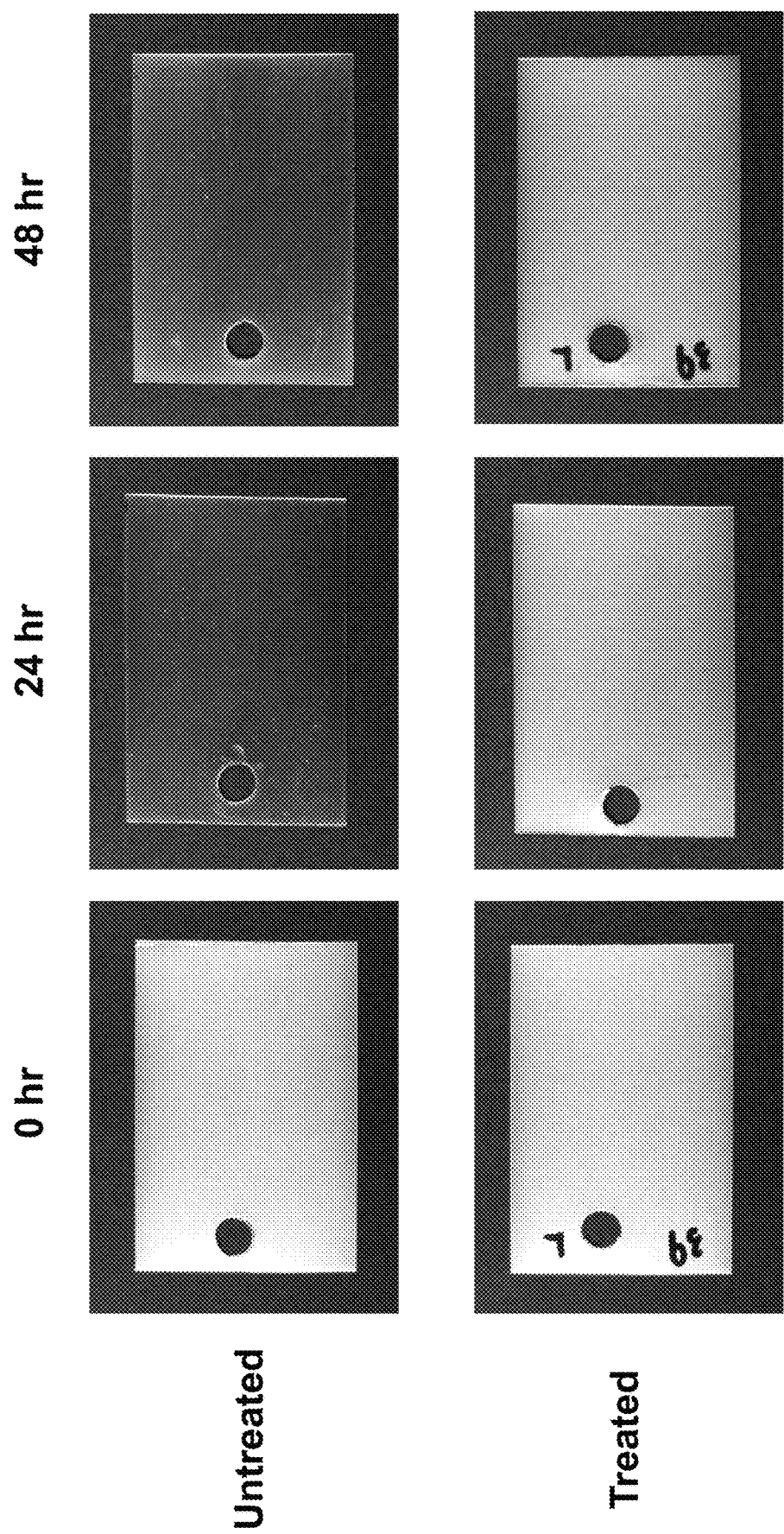
[Fig. 2]

[Fig. 3]
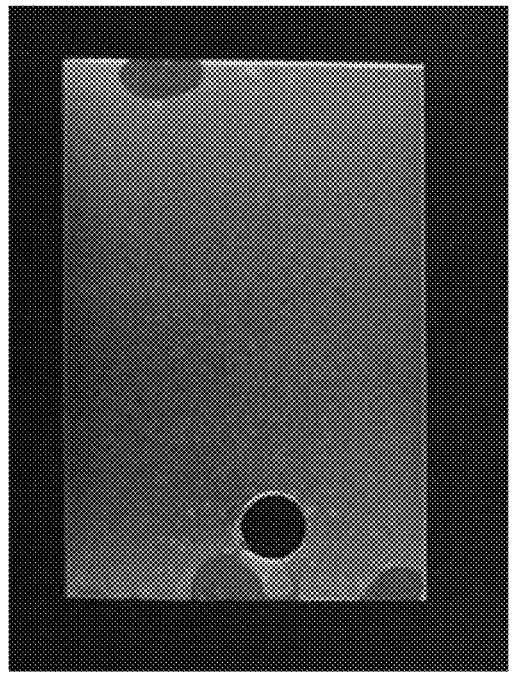
Treated Au plate
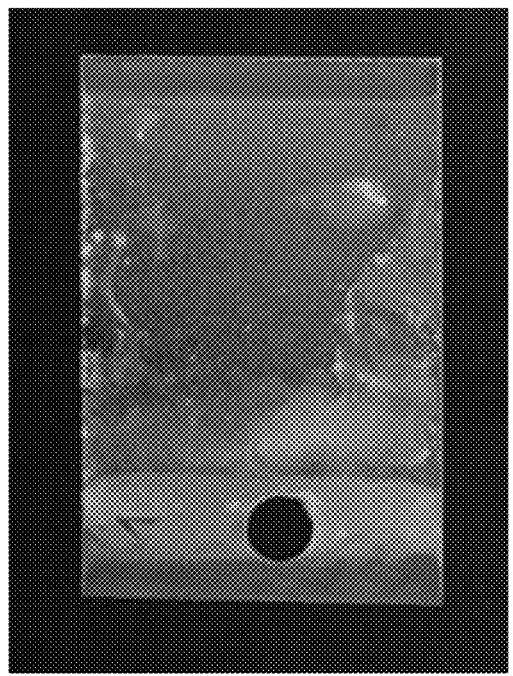
Untreated Au plate

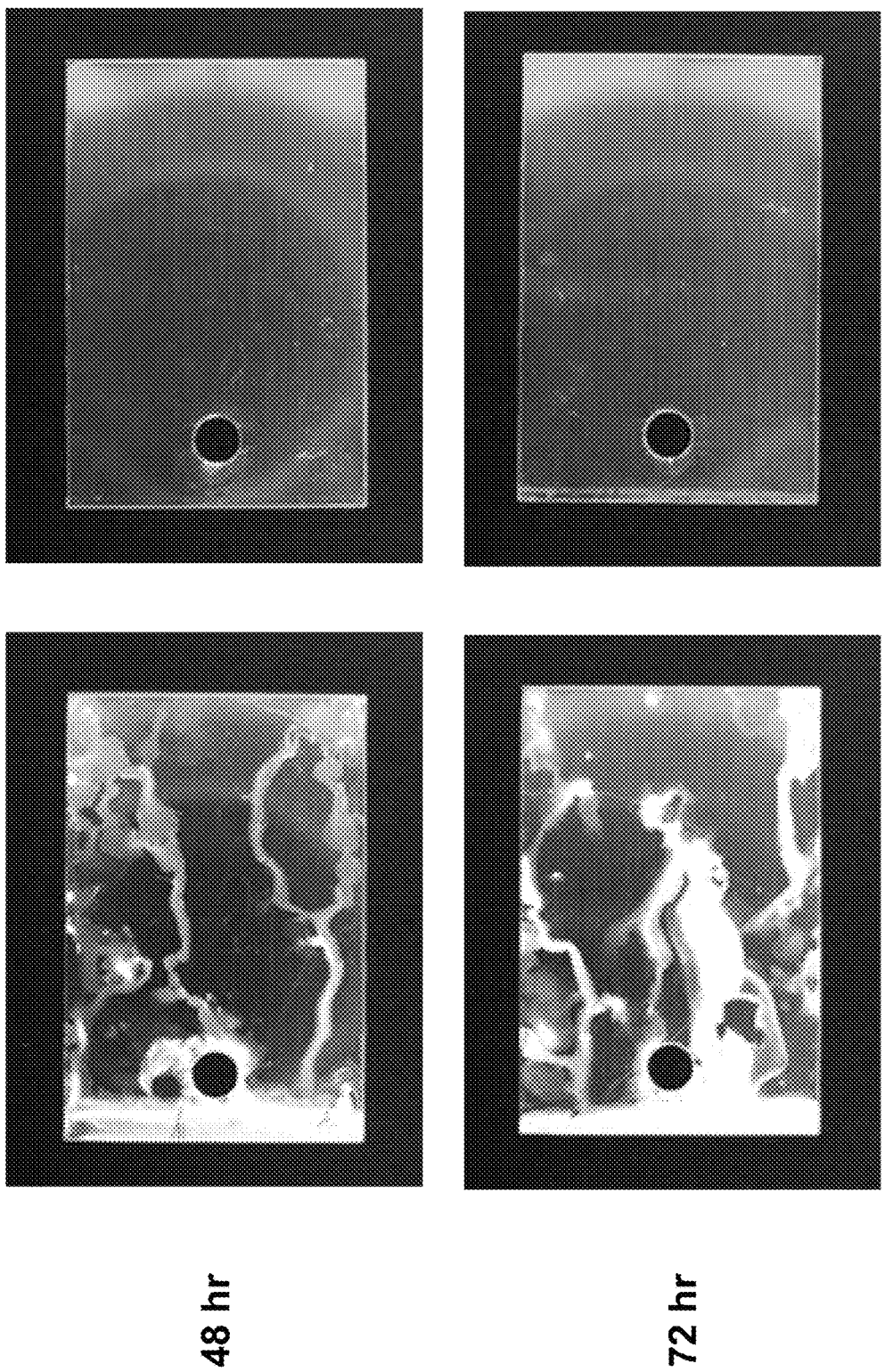
[Fig. 4]

HYDROPHILIC METAL SURFACE TREATMENT AGENT

TECHNICAL FIELD

The present invention relates to a hydrophilic metal surface treatment agent by which a water-repellent property can be given to a metal surface with suppressing a corrosion and a discolorment of the metal, a method for treating a surface of a metal by using the hydrophilic metal surface treatment agent, a synthetic intermediate compound of a branched glycerol derivative as an active ingredient of the hydrophilic metal surface treatment agent, and a method for efficiently producing the synthetic intermediate compound.

BACKGROUND ART

In recent years, properties not found in the past, such as a thinning, a miniaturization and a densification with a number of devices of an electronic equipment, has been further required in an electronics field, since a developed IoT technology is applied to broader range of products and the number of parts is increased with an electronification of on-vehicle members in the automotive industry.

A surface treatment technique to control the properties of a base material surface plays an important role to maintain an excellent electrical property, a high reliability and a high corrosion resistance of electrical parts.

An example of a technique to inhibit a decrease of an electrical property and an appearance deterioration caused by a corrosion of a metal base material due to oxidation and sulfurization among various surface treatment techniques includes a method for forming a coating membrane on a base material metal surface. Both of an organic material and an inorganic material are used as a raw material of such a coating membrane. A raw material of a self-assembled monolayer, i.e. SAM, among such raw materials is variously studied. In particular, alkanethiols have been conventionally and variously studied and utilized as a compound to form SAM. For example, Patent document 1 discloses a method for forming a self-assembled monolayer composed of an alkanethiol on a metal base material surface by immersing the metal base material in an organic solvent solution of a linear alkanethiol. Patent document 2 discloses a functional metal composite substrate in which a SAM membrane composed of alkanethiol or the like is formed on a surface of a metal composite raw material.

Since an alkanethiol is lipophilic and is not dissolved in water, an organic solvent must be used for forming SAM on a metal surface. On the one hand, water is recently required to be used in place of an organic solvent in terms of decrease of an environmental load. For example, Patent document 3 discloses an aqueous sealing treatment agent containing an inhibitor such as a benzotriazole compound, a surfactant and an amine compound. Patent document 4 discloses a method for forming a coating membrane on a silver-coated surface of a metal material by contacting a surface treatment agent aqueous solution in which 6-anilino-1,3,5-triazine-2,4-dithiol and/or an alkali metal salt thereof is dissolved or dispersed in water with the silver-coated metal material. Though it is described in Patent document 3 that a formed coating membrane is water-repellent, the water repellency is qualitatively evaluated. In addition, the water repellency and corrosion resistance may not be sufficient, since the active ingredient is water-soluble.

The inventors of the present invention developed a branched glycerol structure to improve a water solubility of a compound (Patent document 5). Also, the present inventors developed the following branched glycerol trimer as a synthetic intermediate compound to form the branched glycerol structure (Patent document 6 and Non-patent document 1).

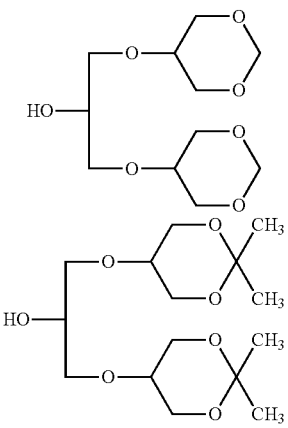

PRIOR ART DOCUMENT

Patent Document

Patent document 1: JP 2001-152363 A
Patent document 2: JP 2010-99817 A
Patent document 3: JP 2003-129257 A
Patent document 4: JP 2015-172214 A
Patent document 5: WO 2004/29018
Patent document 6: JP 2011-178698 A Non-Patent Document Non-patent document 1: HATTORI Hatsuhiko et al., Synthesis, 2012, 44, 2365-2373

DISCLOSURE OF THE INVENTION

Problems to be Solved by the Invention

As described above, an organic solvent must be used as a solvent of a conventional metal surface treatment agent capable of forming a lipophilic coating membrane. In addition, since an active ingredient of a metal surface treatment agent containing water as a solvent is hydrophilic, there is a problem of an endurance of a formed covering membrane.

Furthermore, the present inventors developed two kinds of branched glycerol trimers as a synthetic intermediate compound to introduce a structure to improve a water solubility to a compound, but the dimethyl branched glycerol trimer is difficult to be synthesized. Also, an unsubstituted branched glycerol trimer is difficult to be efficiently synthesized, since a precursor thereof cannot be separated from an impurity. In addition, an unsubstituted branched glycerol trimer is relatively difficult to be deprotected.

Accordingly, the objective of the present invention is to provide a hydrophilic metal surface treatment agent by which a water-repellent property can be given to a metal surface with suppressing a corrosion and a discolorment of the metal, a method for treating a surface of a metal by using the hydrophilic metal surface treatment agent, a synthetic intermediate compound of a branched glycerol derivative as an active ingredient of the hydrophilic metal surface treatment agent, and a method for efficiently producing the synthetic intermediate compound.

Means for Solving the Problems

The inventors of the present invention repeated intensive studies in order to solve the above-described problems. As a result, the inventors completed the present invention by finding that a self-assembled monolayer can be formed by dissolving or dispersing a compound formed by binding a branched glycerol structure and a hydrocarbon group with the specific structure in water and treating a metal surface therewith, and a high water repellency and a corrosion resistance can be given to the metal due to a hydrocarbon of the self-assembled monolayer.

The present invention is hereinafter described.

[1] A hydrophilic metal surface treatment agent comprising a branched glycerol derivative represented by the following formula (I) as an active ingredient:

$$R^1-S-X-Y\left[-O-\underset{-OH}{\overset{-OH}{<}}\right]_n \quad (I)$$

wherein $R^1$ is a hydrocarbon group having a carbon number of 10 or more and 30 or less, X is S or a carbonyl group, Y is an n+1 valent linker group, n is an integer of 1 or more and 5 or less.

[2] The hydrophilic metal surface treatment agent according to the above [1], comprising water as a solvent.

[3] The hydrophilic metal surface treatment agent according to the above [2], wherein a concentration of the branched glycerol derivative represented by the formula (I) is 0.005 mM or more and 5 mM or less.

[4] The hydrophilic metal surface treatment agent according to the above [2], wherein a concentration of the branched glycerol derivative represented by the formula (I) is 0.001 mass % or more and 5 mass % or less.

[5] The hydrophilic metal surface treatment agent according to any one of the above [1] to [4], further comprising an alkaline agent.

[6] The hydrophilic metal surface treatment agent according to any one of the above [1] to [5], further comprising a surfactant.

[7] A method for treating a surface of a metal, comprising the step of treating the surface of the metal by using the hydrophilic metal surface treatment agent according to any one of the above [1] to [6].

[8] The method according to the above [7], wherein the surface of the metal is treated by immersing the metal in the hydrophilic metal surface treatment agent in liquid form, applying the hydrophilic metal surface treatment agent to the surface of the metal, or spraying the hydrophilic metal surface treatment agent on the surface of the metal.

[9] The method according to the above [7] or [8], wherein the metal is gold, silver, platinum, palladium, tin, aluminum, nickel, iron, copper, zinc or an alloy thereof.

[10] A protected branched glycerol derivative represented by the following formula (II):

(II)

wherein $R^2$ is a $C_{1-6}$ alkyl group.

[11] A method for producing a protected branched glycerol derivative represented by the above formula (II), the method comprising the steps of:

reacting glycerin with an aldehyde compound $R^2$—CHO to obtain a mixture comprising the compounds represented by the following formulae (III-1) to (III-4):

(III-1)

(III-2)

(III-3)

(III-4)

wherein $R^2$ has the same meaning as the above, purifying the compound represented by the formula (III-1) from the mixture by distillation, and reacting the compound represented by the formula (III-1) with an epihalohydrin to obtain the protected branched glycerol derivative represented by the formula (II).

[12] Use of a branched glycerol derivative represented by the formula (I) for treating a surface of a metal.

[13] The use according to the above [12], wherein a hydrophilic metal surface treatment agent comprising the branched glycerol derivative represented by the above formula (I) and water as a solvent.

[14] The use according to the above [13], wherein a concentration of the branched glycerol derivative represented by the above formula (I) is 0.005 mM or more and 5 mM or less.

[15] The use according to the above [13], wherein a concentration of the branched glycerol derivative represented by the formula (I) is 0.001 mass % or more and 5 mass % or less.

[16] The use according to any one of the above [12] to [15], wherein the hydrophilic metal surface treatment agent further comprises an alkaline agent.

[17] The use according to any one of the above [12] to [16], wherein the hydrophilic metal surface treatment agent further comprises a surfactant.

Effect of the Invention

Many of conventional alkanethiol compounds to form a self-assembled monolayer on a metal surface are dissolved in an organic solvent to be used, since a water solubility thereof is low due to a long chain alkyl group having the carbon number of, for example, 8 or more. On the one hand, water, which is hydrophilic and which is environmentally friendly, can be used as a solvent for the branched glycerol derivative of the present invention. In addition, the branched glycerol structure is cleaved by drying to form a self-assembled monolayer. Since the self-assembled monolayer is composed of a long chain hydrocarbon, the self-assembled monolayer is excellent in a water repellency and a corrosion resistance. The hydrophilic metal surface treatment agent of the present invention, therefore, is industrially very useful, since the surface texture of a metal can be effectively improved by the hydrophilic metal surface treatment agent.

BRIEF DESCRIPTION OF THE DRAWINGS

FIG. 1 are photographs of metal samples treated by the hydrophilic metal surface treatment agent of the present invention and untreated metal samples, after the samples were immersed in a potassium sulfide aqueous solution for a predetermined time.

FIG. 2 are photographs of metal samples treated by the hydrophilic metal surface treatment agent of the present invention and untreated metal samples, after the samples were exposed to hydrogen sulfide gas for a predetermined time.

FIG. 3 are photographs of an Au coated sample treated by the hydrophilic metal surface treatment agent of the present invention and an untreated Au coated sample, after a sodium chloride aqueous solution was sprayed thereon for a predetermined time.

FIG. 4 are photographs of Ag coated samples treated by the hydrophilic metal surface treatment agent of the present invention and untreated Ag coated samples, after a sodium chloride aqueous solution was sprayed thereon for a predetermined time.

MODE FOR CARRYING OUT THE INVENTION

The hydrophilic metal surface treatment agent of the present invention comprises the branched glycerol derivative represented by the following formula (I) as an active ingredient. Hereinafter, the compound is abbreviated as "the branched glycerol derivative (I)".

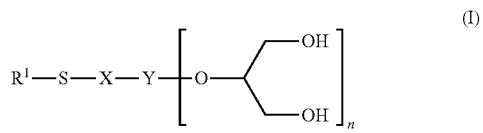

In the formula (I), $R^1$ is a hydrocarbon group having the carbon number of 10 or more and 30 or less. An example of the hydrocarbon group includes a $C_{10-30}$ alkyl group, a $C_{10-30}$ alkenyl group, a $C_{10-30}$ alkynyl group, a $C_{10-30}$ aryl group and a $C_{10-30}$ arylalkyl group. When the carbon number is 10 or more, a self-assembled monolayer excellent in a water repellency can be formed on a metal surface more surely and a protection of the metal surface becomes possible. On the one hand, when the carbon number is 30 or less, the water solubility of the branched glycerol derivative (I) can be ensured more surely. The carbon number is preferably 12 or more, more preferably 14 or more, even more preferably 16 or more, and preferably 24 or less, more preferably 22 or less, even more preferably 20 or less.

The "$C_{10-30}$ alkyl group" means a linear or branched monovalent saturated aliphatic hydrocarbon group having the carbon number of 10 or more and 30 or less, and is exemplified by decyl, dodecyl, tetradecyl, hexadecyl, octadecyl, icosyl, docosyl, tetracosyl, hexacosyl, octacosyl and triacontyl. The $C_{10-30}$ alkyl group is preferably a $C_{12-24}$ alkyl group, more preferably a $C_{14-22}$ alkyl group, and even more preferably $C_{16-20}$ alkyl group.

The "$C_{10-30}$ alkenyl group" means a linear or branched monovalent unsaturated aliphatic hydrocarbon group of which carbon number is 10 or more and 30 or less and which has at least one carbon-carbon double bond, and is exemplified by decenyl, dodecenyl, tetradecenyl, hexadecenyl, octadecenyl, icosenyl, docosenyl, tetracosenyl, hexacosenyl, octacosenyl and triacontenyl. The $C_{10-30}$ alkenyl group is preferably a $C_{12-24}$ alkenyl group, more preferably a $C_{14-22}$ alkenyl group, and even more preferably a $C_{16-20}$ alkenyl group.

The "$C_{10-30}$ alkynyl group" means a linear or branched monovalent unsaturated aliphatic hydrocarbon group of which carbon number is 10 or more and 30 or less and which has at least one carbon-carbon triple bond, and is exemplified by decynyl, dodecynyl, tetradecynyl, hexadecynyl, octadecynyl, icosynyl, docosynyl, tetracosynyl, hexacosynyl, octacosynyl and triacontynyl. The $C_{10-30}$ alkynyl group is preferably a $C_{12-24}$ alkynyl group, more preferably a $C_{14-22}$ alkynyl group, and even more preferably a $C_{16-20}$ alkynyl group.

The "$C_{10-30}$ aryl group" means a monovalent aromatic hydrocarbon group having the carbon number of 10 or more and 30 or less, and is exemplified by naphthyl, biphenyl, phenanthrenyl, anthracenyl, triphenylenyl, pyrenyl, naphthacenyl, pentacenyl, hexacenyl and heptacenyl.

The "$C_{10-30}$ arylalkyl group" is exemplified by an alkyl group having a $C_{6-12}$ aryl group at the S-side end, the most end and the intermediate portion. An example of the $C_{6-12}$ aryl group includes phenyl, naphthyl, indenyl and biphenyl.

The X in the formula (I) is S or a carbonyl group. In other words, the X forms a disulfide bond (—S—S—) or a thioester group (—S—C(═O)—) with the adjacent S. Since a metal generally has a high affinity for a thiol group (—SH), the disulfide bond or thioester group is cleaved to form a self-assembled monolayer of $R^1$—S— on a metal surface by treating the metal surface with the hydrophilic metal surface treatment agent of the present invention.

The Y in the formula (I) is an n+1 valent linker group to bind n-tuple branched glycerol structures to the X and has the function to facilitate the synthesis of the branched glycerol derivative (I). The linker group is not particularly restricted as long as the linker group has such a function and is exemplified by a $C_{1-6}$ alkanediyl group, a $C_{1-6}$ alkanetriyl group, an ether group (—O—), a carbonyl group (—C(=O)—), an ester group (—O—C(=O)— or —C(=O)—O—), an amide group (—NH—C(=O)— or —C(=O)—NH—), a urea group (—NH—C(=O)—NH—), a polyalkylene glycol group and a polyvinyl alcohol group; and a group formed by binding 2 or more and 5 or less of the groups. An example of the bound group includes a $C_{1-6}$ alkanediyl group having a group selected from an ether group, a carbonyl group, an ester group, an amide group, a urea group, a polyalkylene glycol group and a polyvinyl alcohol group at one end or both ends and/or an intermediate portion; and a $C_{1-6}$ alkanetriyl group having a group selected from an ether group, a carbonyl group, an ester group, an amide group, a urea group, a polyalkylene glycol group and a polyvinyl alcohol group at 1 or more and 3 or less of the ends and/or an intermediate portion.

The branched glycerol derivative (I) may have a dendrimer structure formed by binding two branched glycerol units with a glycerol structure. Such a dendrimer structure is exemplified as follows. The left side structure is a dendrimer structure wherein n=2 and Y is a trivalent linker group, and the right side structure is a dendrimer structure wherein n=4 and Y is a pentavalent linker group.

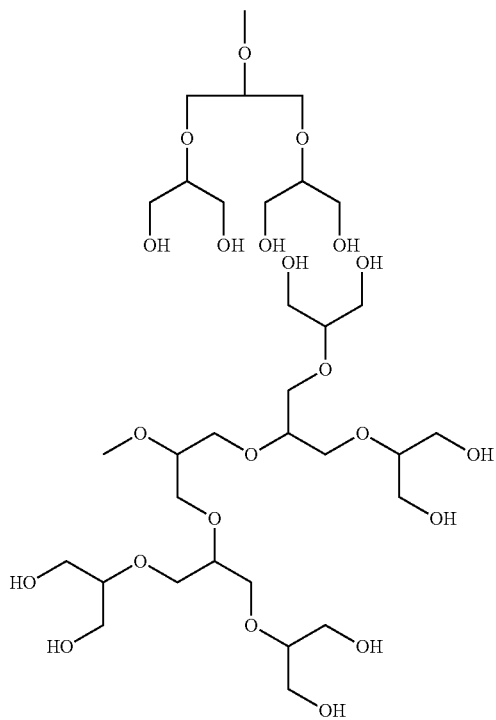

The structure in brackets in the formula (I) is referred to as "the branched glycerol unit" in some cases. The n in the formula (I) is the number of the branched glycerol unit and is an integer of 1 or more and 5 or less. When the n is 1 or more, the hydrophilicity of the branched glycerol derivative (I) can be ensured, and when the n is 5 or less, the cost to produce the branched glycerol derivative (I) can be effectively controlled. The n is preferably 2 or more, and preferably 4 or less and more preferably 2.

A person skilled in the art can readily synthesize the branched glycerol derivative (I), since the branched glycerol derivative (I) has a relatively simple structure. For example, the branched glycerol derivative (I) can be synthesized by reacting a compound having a protected branched glycerol structure and a compound having a long chain alkyl group $R^1$ to form a —S—X— group and the ester group or the amide group in the linker group. The production method to form a thioester group in the case where the X is a carbonyl group and the production method to form the ester group in the linker group are described as follows. A condensating agent may be used and a carboxy group may be active-esterized in order to form a thioester group and an ester group. Finally the branched glycerol structure may be deprotected in an acidic condition.

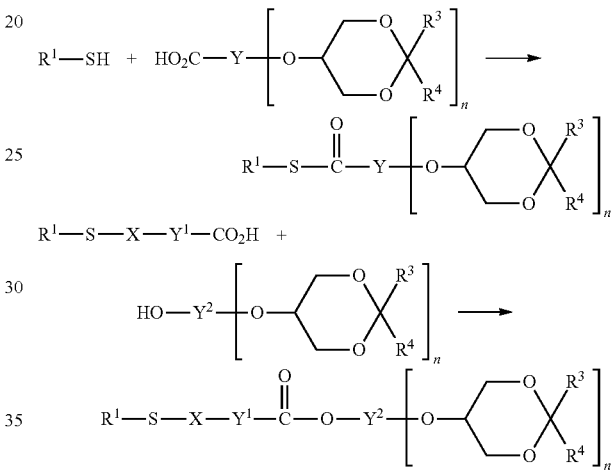

wherein $R^1$, X, Y and n have the same meanings as the above, $R^3$ and $R^4$ are independently H or a $C_{1-6}$ alkyl group, $Y^1$ and $Y^2$ form a linker group Y as $Y^1$—C(=O)—$Y^2$.

The "$C_{1-6}$ alkyl group" is a linear or branched monovalent saturated aliphatic hydrocarbon group having the carbon number of 1 or more and 6 or less, and is exemplified by methyl, ethyl, n-propyl, isopropyl, n-butyl, isobutyl, s-butyl, t-butyl, n-pentyl and n-hexyl. The $C_{1-6}$ alkyl group is preferably a $C_{1-4}$ alkyl group, more preferably a $C_{1-2}$ alkyl group, and even more preferably methyl.

It is preferred that one of $R^3$ and $R^4$ is H and the other is a $C_{1-6}$ alkyl group. With respect to the protective group of the branched glycerol unit, a protective group of which both of $R^3$ and $R^4$ are $C_{1-6}$ alkyl groups can be cleaved in the mildest condition, and as a result, the protective group can be cleaved without impacting on the S—X bond. On the one hand, the protective group of which both of $R^3$ and $R^4$ are H is the most difficult to be cleaved, and the easiness to cleave the protective group of which one of $R^3$ and $R^4$ is H and the other is a $C_{1-6}$ alkyl group is included between those of the above-described protective groups. When a 5-hydroxy-1,3-dioxane compound as a precursor of the branched glycerol unit is synthesized from glycerin and a carbonyl compound as follows, an α,α'-isomer and an α,β-isomer are generated, but when $R^3$ and $R^4$ are $C_{1-6}$ alkyl groups, only an α,β-isomer as a side product is generated due to a steric effect (Patent document 6 and Non-patent document 1). Accordingly, a branched glycerol trimer of which $R^3$ and $R^4$ are $C_{1-6}$ alkyl groups is synthesized by transforming the protective group of a branched glycerol trimer of which $R^3$ and $R^4$ are H (Patent document 6 and Non-patent document 1). On the one hand, when glycerin and formaldehyde are reacted, an α,α'-isomer and an α,β-isomer are generated in a ratio of 55:45 to 60:40 (Non-patent document 1). The isomers are needed to be esterified with pivalic acid, since the isomers cannot be directly separated (Patent document 6 and Non-patent document 1). In other words, an esterification step and a hydrolysis step are superfluously required.

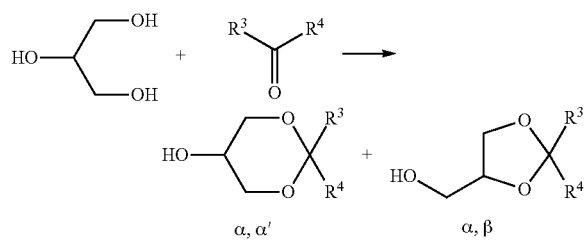

On the one hand, with respect to the protected branched glycerol derivative, hereinafter referred to as "protected branched glycerol derivative (II)", of which one of $R^3$ and $R^4$ is H and the other is a $C_{1-6}$ alkyl group, 4 isomers, i.e. trans-α,α'-isomer, cis-α,α'-isomer, trans-α,β-isomer and cis-α,β-isomer, are generated from glycerin and a ketone compound, and only the cis-α,α'-isomer can be directly separated from the other isomers by distillation. In addition, the protected branched glycerol derivative (II) can be deprotected in a relatively mild condition. The protected branched glycerol derivative (II), therefore, is very useful as a synthetic intermediate of the branched glycerol derivative (I).

The protected branched glycerol derivative (II) can be synthesized by reacting the cis-α,α'-isomer of which one of $R^3$ and $R^4$ is H and the other is a $C_{1-6}$ alkyl group, i.e. cis-5-hydroxy-2-$C_{1-6}$ alkyl-1,3-dioxane, and an epihalohydrin. An example of an epihalohydrin includes epichlorohydrin, epibromohydrin and epiiodohydrin.

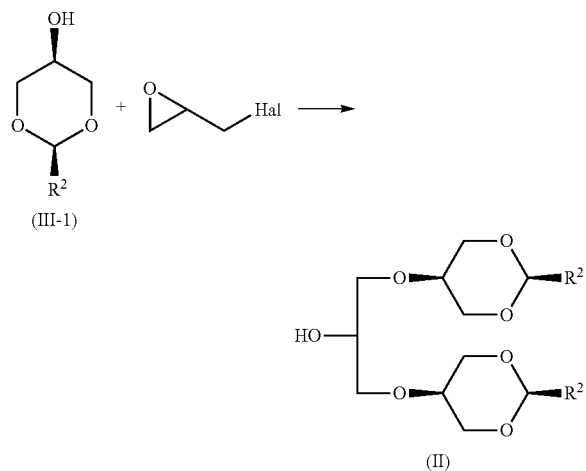

wherein Hal is chloro, bromo or iodo.

The hydrophilic metal surface treatment agent of the present invention may not contain a solvent and may be dissolved or dispersed in a solvent to be a solution or a dispersion for use. The concentration of the branched glycerol derivative (I) in the solid hydrophilic metal surface treatment agent of the present invention in such a case is preferably 60 mass % or more or 70 mass % or more, more preferably 80 mass % or more or 90 mass % or more, and even more preferably 95 mass % or more or 98 mass % or more. The upper limit of the above concentration is not particularly restricted, and the solid hydrophilic metal surface treatment agent is preferably composed of the branched glycerol derivative (I) other than an unavoidable impurity and an unavoidable contaminant. In other words, the above concentration is preferably 100 mass % or less.

The solvent of the hydrophilic metal surface treatment agent according to the present invention is preferably water in terms of a safety and an environmental burden. A concentration of the branched glycerol derivative (I) in the hydrophilic metal surface treatment agent of the present invention which contains water as a solvent may be 0.005 mM or more and 5 mM or less and 0.001 mass % or more and 5 mass % or less. When the concentration is 0.005 mM or more or 0.001 mass % or more, a self-assembled monolayer may be formed on a metal surface more surely. On the one hand, when the concentration is 5 mM or less or 5 mass % or less, the branched glycerol derivative (I) may be effectively dissolved or dispersed. The concentration is more preferably 0.01 mM or more or 0.005 mass % or more, and more preferably 1 mM or less or 1 mass % or less, even more preferably 0.1 mM or less or 0.1 mass % or less. In addition, a solution of the branched glycerol derivative (I) having a relatively high concentration may be shipped out as the hydrophilic metal surface treatment agent and diluted for use in terms of a haulage cost.

The hydrophilic metal surface treatment agent of the present invention may contain an alkaline agent. The alkaline agent accelerates the cleavage of a disulfide group or a thioester group of the branched glycerol derivative (I) and as a result, facilitates the formation of a self-assembled monolayer on a metal surface. The alkaline agent is not particularly restricted as long as the pH of the hydrophilic metal surface treatment agent containing water as a solvent can be adjusted to more than 7 by the alkaline agent. An example of the alkaline agent includes a hydrogencarbonate salt of an alkali metal, such as sodium hydrogencarbonate and potassium hydrogencarbonate; a carbonate salt of an alkali metal, such as sodium carbonate and potassium carbonate; a carbonate salt of an alkaline earth metal, such as calcium carbonate; a hydroxide of an alkali metal, such as sodium hydroxide and potassium hydroxide; ammonia; an organic base such as triethylamine, N,N-diisopropylethylamine, triethanolamine and pyridine.

A concentration of the alkaline agent in the hydrophilic metal surface treatment agent according to the present invention may be appropriately adjusted, and for example, the concentration in the hydrophilic metal surface treatment agent containing water as a solvent may be adjusted to 0.001 mass % or more and 5 mass % or less.

The hydrophilic metal surface treatment agent of the present invention may contain a surfactant. Such a surfactant has a function to stabilize the liquid hydrophilic metal surface treatment agent by improving a solubility and a dispersibility of the branched glycerol derivative (I). As the surfactant, any of a non-ionic surfactant, an anion surfactant, a cation surfactant and a zwitterionic surfactant can be used.

An example of a non-ionic surfactant includes a polyoxyethylene alkylamine such as POE laurylamine; a polyoxyethylene alkyl ether such as POE lauryl ether and POE cetyl ether; a glycerin fatty acid ester such as glyceryl monostearate; and a sorbitan fatty acid ester such as sorbitan monolaurate. The "POE" is an abbreviation for polyoxyethylene.

An example of an anion surfactant includes an alkyl sulfate ester salt such as sodium lauryl sulfate, potassium lauryl sulfate, ammonium lauryl sulfate, magnesium lauryl sulfate, monoethanolamine lauryl sulfate, sodium myristyl sulfate, sodium stearyl sulfate and sodium oleyl sulfate; an alkyl ether sulfate ester salt such as POE (2) sodium lauryl ether sulfate and POE (3) sodium myristyl ether sulfate; an N-acyl methyl taurine salt such as potassium methyl cocoyl taurate and sodium methyl lauroyl taurate; an N-acyl glutamate salt such as cocoyl glutamate; an N-acyl methylalanine salt such as sodium lauroyl methylalanine; an N-acyl sarcosinate salt such as sodium lauroyl sarcosinate; an acyl lactate salt such as sodium stearoyl lactate; and a fatty acid salt such as potassium coconut oil fatty acid salt, potassium laurate and triethanolamine laurate. The "POE" is an abbreviation for polyoxyethylene, and the number in parentheses is an addition mole number.

An example of a cation surfactant includes an alkyl quaternary ammonium salt such as lauryltrimethylammonium chloride, stearyltrimethylammonium bromide and dicocoyl dimethyl ammonium chloride; and an amine salt such as dimethylstearylamine and stearamidoethyl diethylamine.

An example of a zwitterionic surfactant includes betaine.

A concentration of a surfactant in the hydrophilic metal surface treatment agent of the present invention may be appropriately adjusted, and for example, the concentration in the hydrophilic metal surface treatment agent containing water as a solvent may be adjusted to 0.005 mass % or more and 5 mass % or less.

When a metal surface is treated by using the hydrophilic metal surface treatment agent of the present invention, a self-assembled monolayer is formed on the metal surface and a discolorment and a degeneration such as rusting can be suppressed due to a given water repellency.

An example of the metal includes gold, silver, platinum, palladium, tin, aluminum, nickel, iron, copper, zinc or an alloy thereof. A shape of the metal is not particularly restricted, and a surface may be coated with the metal.

A condition to treat a metal surface by the hydrophilic metal surface treatment agent of the present invention is not particularly restricted. For example, a metal may be immersed in the liquid hydrophilic metal surface treatment agent, or the liquid hydrophilic metal surface treatment agent may be applied to or sprayed on the metal surface. A temperature of the liquid hydrophilic metal surface treatment agent in the case of the immersion may be appropriately adjusted and may be adjusted to, for example, 20° C. or higher and 80° C. or lower. An immersion time may be adjusted to 1 second or longer and 10 hours or shorter. After the liquid hydrophilic metal surface treatment agent is applied or sprayed, the metal may be heated in the above temperature range for a time similar to the above immersion time. A self-assembled monolayer may be formed on a metal surface treated as the above by cleaving the disulfide bond or the thioester group of the hydrophilic metal surface treatment agent. Then, the metal surface may be washed and further dried.

The present application claims the benefit of the priority date of Japanese patent application No. 2019-112183 filed on Jun. 17, 2019. All of the contents of the Japanese patent application No. 2019-112183 filed on Jun. 17, 2019, are incorporated by reference herein.

EXAMPLES

Hereinafter, the examples are described to demonstrate the present invention more specifically, but the present invention is in no way restricted by the examples, and the examples can be appropriately modified to be carried out within a range which adapts to the contents of this specification. Such a modified example is also included in the range of the present invention.

Hereinafter, the "branched glycerol" is abbreviated as "BGL".

Example 1: Production of BGL

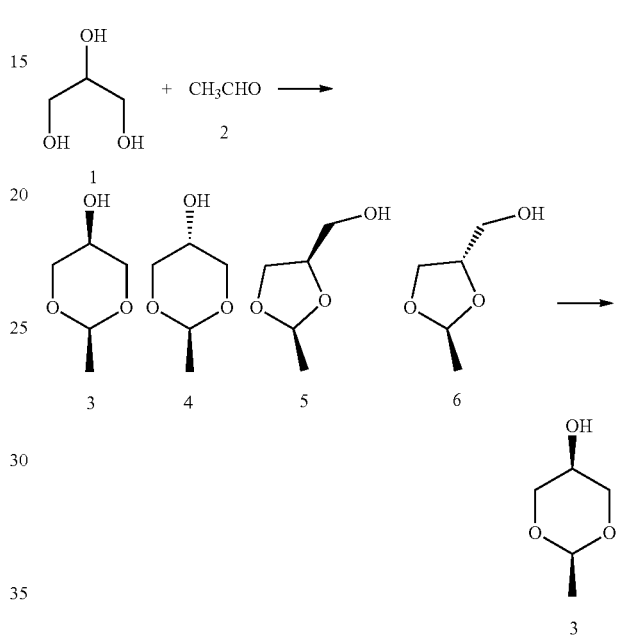

(1) Production of BGL Base Unit

A mixture of glycerin (Compound 1) (48 g, 0.521 mol, 1.0 equivalent), acetaldehyde (Compound 2) (25.26 g, 0.573 mol, 1.1 equivalents) and an ion-exchange resin ("Amberlyst® 17" manufactured by Rohm and Haas) (0.3 g) was stirred at 0° C. Since the mixture was composed of two layers, the mixture was cloudy for first 30 minutes during the stirring. The mixture however gradually became colorless and transparent. The mixture was stirred at 0° C. for the initial period of time, since a balloon filled with argon gas expanded due to vaporized acetaldehyde through inactivity. After a mild exothermic reaction died down after a while, the mixture was stirred at 40° C. for 12 hours. The ion-exchange resin was removed by filtration, and the filtrate was concentrated to obtain a mixture of four colorless and transparent Isomers 3 to 6 (fraction of mixture ratio—about 1:1:1:1 and boiling point: 172 to 185° C./760 mmHg) (yield amount of mixture: 44.10 g, total 0.373 mol, yield of mixture: 71.6%). An amount of a distillation kettle residue was 5.19 g, and the residue was mainly glycerin.

An ion-exchange resin ("Amberlyst® 17" manufactured by Rohm and Haas) (0.3 g) was added to the mixture of the distilled Isomers 3 to 6 (44.10 g, 0.373 mol), and only Isomer 3 was obtained by slowly distilling Isomer 3 under reduced pressure of 30 mmHg (boiling point: 85 to 88° C., yield amount: 38.0 g, 0.369 mol, purity: 99%, yield to 100% of the above mixture: 86%).

(2) Production of BGL Trimer

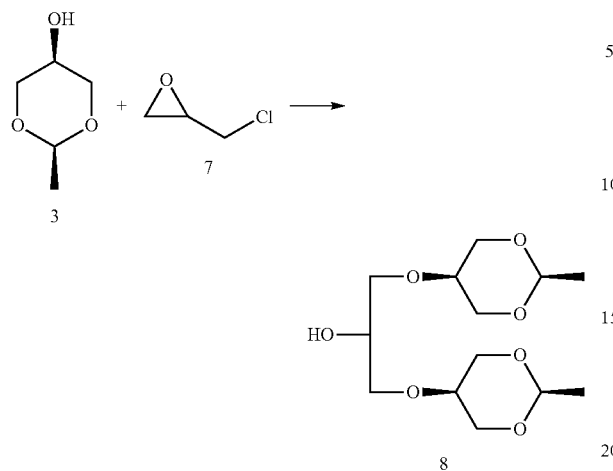

A concentrated aqueous solution prepared by dissolving Isomer 3 (734.60 g, 6.219 mol) and sodium hydroxide (248.74 g, 6.219 mol) in water (about 100 mL) was mixed with tetrabutylammonium bromide (200.47 g, 0.622 mol). While the obtained liquid in an emulsified state was vigorously stirred at room temperature, epichlorohydrin (Compound 7) (143.10 g, 1.555 mol) was added dropwise thereto. The temperature of the mixture was adjusted using ice so that epichlorohydrin was not vaporized nor lost due to the exothermic reaction. After an increase of the temperature was not observed after the dropwise addition, the mixture was stirred at 60° C. for 6 to 24 hours. After the mixture was left to be cooled to room temperature, the obtained reaction mixture was diluted with water and the diluted reaction mixture was added into the other vessel. Ethyl acetate (1 L) was added thereto. The insoluble solid was removed by filtration using cerite and washed using ethyl acetate. The filtrate and the wash liquid were combined, the aqueous phase and the organic phase were separated, and extraction from the aqueous phase was carried out using ethyl acetate (500 mL, 300 mL). The organic phase and the extraction liquid were combined, and the mixture was washed using saturated sodium chloride aqueous solution (200 mL) and dried using anhydrous sodium sulfate (50 g). A low boiling point component such as ethyl acetate was distilled away using an evaporator to obtain a mixed liquid of Compound 8 and the raw material Isomer 3. The obtained mixed liquid was transferred into a distillation still to recover the raw material Isomer 3 (344.95 g, 2.92 mol, 94% could be recovered). The target 1,3-bis(((2S,5s)-2-methyl-1,3-dioxane-5-yl)oxy)propane-2-ol (Compound 8, Mw: 292.33) was obtained by further reduced pressure (yield amount: 385.95 g, 1.32 mol, yield: 85%).

FT-IR (neat): 3477, 2985, 2862, 1645, 1447, 1404, 1340, 1282, 1244, 1153, 1089, 983, 854, 806, 752 $cm^{-1}$ $^1$H NMR (CDCl$_3$, 400 MHz): δ4.73 (q, J=5.2 Hz, 2H), 4.21-4.15 (m, 4H), 4.06 (sext, J=4.8 Hz, 1H), 3.83 (d, J=12.0 Hz, 4H), 3.70 (dd, J=9.6, 4.4 Hz, 2H), 3.64 (dd, J=10.0, 4.4 Hz, 2H), 3.28 (quint, J=2.0 Hz, 2H), 2.86 (d, J=4.8 Hz, 1H), 1.35 and 1.34 (s, 6H)

$^{13}$C NMR (CDCl$_3$, 125 MHz): δ99.20 (CH×2), 71.24 (CH×2), 69.73 (CH), 69.63 (CH$_2$×2), 68.51 (CH$_2$×2), 68.46 (CH$_2$×2), 21.04 (CH$_3$×2)

HRMS (ESI-TOF): Calcd for $C_{13}H_{24}NaO_7^+$ [M+Na]$^+$ requires 315.1420; found 315.1385.

(3) Exchange of Protective Group of BGL Trimer

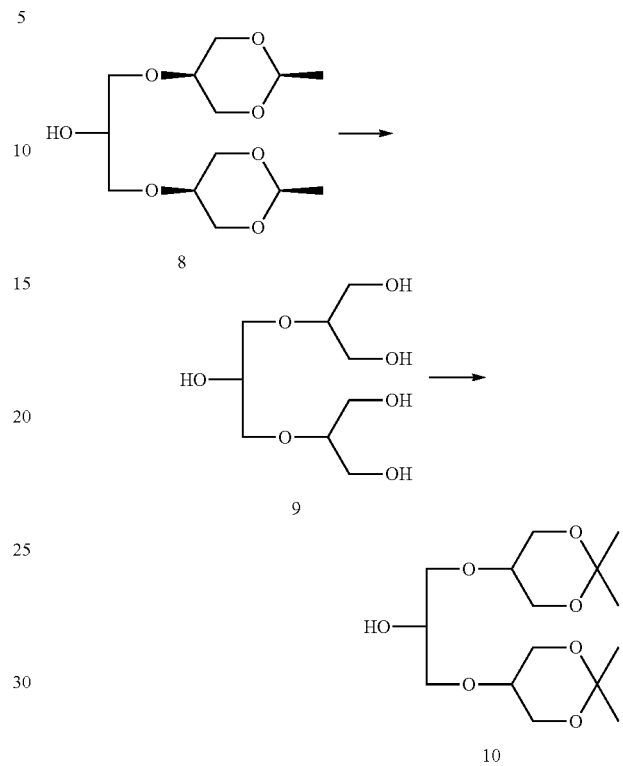

Compound 8 (385.95 g, 1.32 mol) was dissolved in methanol (2000 g, about 2525 mL), and an ion-exchange resin ("Amberlyst®" manufactured by Rohm and Haas) (3.0 g) was added thereto. After the mixture was stirred at 40° C. for 20 hours, the reaction mixture was concentrated under reduced pressure. The concentrate was analyzed by $^1$H NMR; as a result, it was confirmed that Compound 8 was consumed and Compound 9 was generated. The concentrate was immersed in an oil bath warmed to about 80° C. under reduced pressure of about 1 mmHg for a few hours to completely remove methanol. To the obtained highly viscous Compound 9, 2,2-dimethoxypropane (2000 g, 2538 mL) and an ion-exchange resin ("Amberlyst®" manufactured by Rohm and Haas) (3 g) were added. The obtained suspension was stirred at 60° C. for a few hours. Then, the ion-exchange resin was removed by filtration, and potassium carbonate (3 g, 0.028 mol) was added thereto in order to prevent the occurrence of deprotection. The mixture was stirred at room temperature in the same condition for a few tens of minutes and then concentrated using an evaporator. The adherent residual liquid was heated at 1 mmHg and 60° C. for a few hours in order to remove a low boiling point compound. To the residue, 1500 mL of a mixed solvent of hexane/diethyl ether=1000/500 (v/v) was added, and an insoluble component was removed by filtration. The filtrate was left to stand at 4° C. for a few hours, and the deposited crystal of Compound 10 was obtained by filtration. Recrystallization from the remaining liquid was conducted once more using a mixed solvent of hexane (500 mL) and diethyl ether (250 mL) at 4° C. to obtain 1,3-bis((2,2-dimethyl-1,3-dioxane-5-yl)oxy)propane-2-ol (Compound 10) (Mw: 320.38) (yield amount 253.74 g, 0.792 mol, yield: 60%).

Example 2: Production of Hydrophilic Metal Surface Treatment Agent (1) Reaction of Higher Linear Thiol and Succinic Anhydride

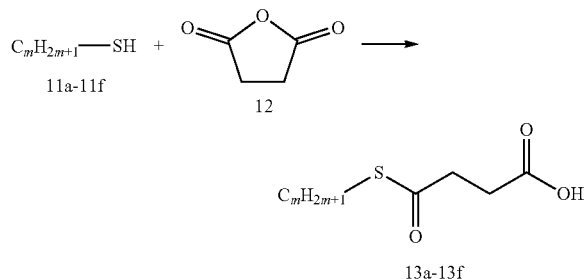

Each alkane thiol (11a to 11f) (4.90 mmol, 1.00 eq) was dissolved in pyridine (9.80 mL, 9.62 g, 122 mmol). The carbon numbers of the alkane thiols 11a to 11f were respectively 12, 14, 16, 18, 20 and 22. While each solution was stirred, succinic anhydride (Compound 12) (0.735 g, 7.35 mmol, 1.50 eq) was slowly added in a few additions. The solution after the mixing was stirred at 40 to 50° C. for 21 to 48 hours, and then 5% potassium hydrogensulfate aqueous solution (500 mL, 25 g (183 mmol) of potassium hydrogensulfate was contained) was added thereto. Extraction from the suspension was conducted two times using ethyl acetate (100 mL). The extraction liquid was dried using anhydrous sodium sulfate (5 g), and the organic solvent was distilled away under reduced pressure to obtain 4-alkylthio-4-oxobutyric acid (13a to 13f) (yield amount: 4.28 to 4.73 mmol, yield: 87 to 96%).

[13a]

FT-IR (KBr): 3422, 2926, 2844, 1719, 1688, 1612, 1556, 1506, 1462, 1412, 1311, 1217, 1104 $cm^{-1}$ $^1$H NMR (CDCl$_3$, 400 MHz): 52.90-2.93 (m, 4H), 2.71-2.75 (m, 2H), 1.59 (q, J=2.4 Hz, 2H), 1.28 (s, br, 18H), 0.91 (t, J=7.2 Hz, 3H)

$^{13}$C NMR (CDCl$_3$, 125 MHz): δ197.79 (C, S—C=O), 178.00 (C, CO$_2$H), 38.11 (CH$_2$), 31.91 (CH$_2$), 29.62 (CH$_2$×2), 29.57 (CH$_2$), 29.46 (CH$_2$×2), 29.34 (CH$_2$) 29.1 (CH$_2$×2) 29.00 (CH$_2$), 28.82 (CH$_2$), 22.68 (CH$_2$) 14.10 (CH$_3$)

HRMS (ESI-TOF) m/z calcd for C$_{16}$H$_{30}$O$_3$SNa [M+Na]$^+$ 325.1813, found 325.1837.

[13b]

FT-IR (KBr): 3359, 2951, 2920, 2850, 1713, 1688, 1462, 1412, 1305, 1217, 1079, 1003, 897, 715 $cm^{-1}$ $^1$H NMR (CDCl$_3$, 400 MHz): δ2.92 (t, J=7.6 Hz, 4H), 2.73 (t, J=6.8 Hz, 2H), 1.59 (q, J=7.2 Hz, 2H), 1.28 (s, br, 22H), 0.90 (t, J=6.8 Hz, 3H)

$^{13}$C NMR (CDCl$_3$, 125 MHz): δ197.79 (C, S—C=O), 177.64 (C, CO$_2$H), 38.13 (CH$_2$), 31.92 (CH$_2$), 29.67 (CH$_2$), 29.66 (CH$_2$), 29.64 (CH$_2$), 29.57 (CH$_2$), 29.47 (CH$_2$×2), 29.35 (CH$_2$), 29.10 (CH$_2$), 29.01 (CH$_2$), 28.96 (CH$_2$), 28.90 (CH$_2$), 28.82 (CH$_2$), 22.69 (CH$_2$), 14.11 (CH$_3$)

HRMS (ESI-TOF) m/z calcd for C$_{18}$H$_{35}$O$_3$S [M+H]$_+$ 331.2307, found 331.2325.

[13c]

FT-IR (KBr): 3422, 2954, 2919, 2850, 1714, 1693, 1633, 1608, 1458, 1408, 1320, 1227, 1087, 1001 $cm^{-1}$ $^1$H NMR (CDCl$_3$, 400 MHz): δ2.90-2.94 (m, 4H), 2.73 (t, J=7.2 Hz, 2H), 1.59 (q, J=7.2 Hz, 2H), 1.28 (s, br, 26H), 0.91 (t, J=7.2 Hz, 3H)

$^{13}$C NMR (CDCl$_3$, 125 MHz): δ197.79 (C, S—C=O), 177.74 (C, CO$_2$H) 38.12 (CH$_2$), 31.92 (CH$_2$), 29.69 (CH$_2$× 2), 29.65 (CH$_2$) 29.63 (CH$_2$) 29.57 (CH$_2$), 29.47 (CH$_2$×2) 29.36 (CH$_2$), 29.10 (CH$_2$), 29.01 (CH$_2$) 28.97 (CH$_2$×2) 28.91 (CH$_2$), 28.83 (CH$_2$), 22.69 (CH$_2$), 14.11 (CH$_3$)

HRMS (ESI-TOF) m/z calcd for C$_{20}$H$_{38}$O$_3$S [M]$^+$ 358.2542, found 358.2505.

[13d]

FT-IR (neat): 3417, 2921, 2850, 2360, 2341, 1716, 1693, 1635, 1462, 1411, 1321, 1222, 1087, 1004 $cm^{-1}$ $^1$H NMR (CDCl$_3$, 500 MHz): δ4.78 (brs, 1H, CO$_2$H), 2.889 (t, J=7.5 Hz, 2H, CH$_2$—S—C=O) 2.886 (t, J=7 Hz, 2H, S—C=O—CH$_2$) 2.70 (t, J=7 Hz, 2H, CH$_2$CO$_2$H) 1.56 (quint, J=7.5 Hz, SCH$_2$CH$_2$CH$_2$), 1.38-1.25 (m, 30H, alkylic CH$_2$), 0.88 (t, J=7 Hz, 3H, CH$_3$)

$^{13}$C NMR (CDCl$_3$, 125 MHz): δ197.9 (C, S—C=O), 176.1 (C, CO$_2$H), 38.2 (CH$_2$), 31.9 (CH$_2$), 29.68 (CH$_2$×5), 29.65 (CH$_2$×2), 29.59 (CH$_2$) 29.49 (CH$_2$×2), 29.37 (CH$_2$) 29.1 (CH$_2$) 29.0 (CH$_2$) 28.8 (CH$_2$×2), 22.7 (CH$_2$), 14.1 (CH$_3$)

HRMS (ESI-TOF) m/z calcd for C$_{22}$H$_{42}$O$_3$SNa [M+Na]$^+$ 409.2752, found 409.2766.

[13e]

FT-IR (KBr): 3406, 2961, 2920, 2842, 1721, 1693, 1462, 1420, 1320, 1227, 1086, 1000, 901, 788, 731, 650 $cm^{-1}$ $^1$H NMR (CDCl$_3$, 400 MHz): δ2.93-2.90 (m, 4H, CH$_2$S and SCOCH$_2$), 2.73 (t, J=7.2 Hz, 2H, CH$_2$CO$_2$H) 1.59 (quint, J=7.6 Hz, SCH$_2$CH$_2$CH$_2$) 1.38-1.28 (m, 34H, alkylic, CH$_2$) 0.91 (t, J=7.2 Hz, 3H, CH$_3$)

$^{13}$C NMR (CDCl$_3$, 125 MHz): δ197.84 (C, S—C=O), 176.63 (C, CO$_2$H) 38.15 (CH$_2$), 31.92 (CH$_2$), 29.70 (CH$_2$× 6), 29.67 (CH$_2$×2) 29.64 (CH$_2$), 29.58 (CH$_2$), 29.47 (CH$_2$×2) 29.36 (CH$_2$), 29.10 (CH$_2$×2), 29.01 (CH$_2$) 28.83 (CH$_2$×2), 22.69 (CH$_2$), 14.11 (CH$_3$)

HRMS (ESI-TOF) m/z calcd for C$_{24}$H$_{47}$O$_3$S [M+H]$^+$ 415.3246, found 415.3245.

[13f]

FT-IR (KBr): 3406, 2954, 2917, 2848, 1714, 1689, 1646, 1621, 1465, 1445, 1408, 1320, 1220, 1087, 1001, 901, 788, 725 $cm^{-1}$ $^1$H NMR (CDCl$_3$, 400 MHz): δ2.92 (t, J=7.2 Hz, 4H) 2.72-2.75 (m, 2H), 1.59 (q, J=6.8 Hz, 2H), 1.28 (m, 38H), 0.91 (t, J=7.2 Hz, 3H)

$^{13}$C NMR (CDCl$_3$, 125 MHz): δ197.84 (C, S—C=O), 176.63 (C, CO$_2$H) 38.17 (CH$_2$), 31.93 (CH$_2$), 29.70 (CH$_2$× 8), 29.66 (CH$_2$×2) 29.58 (CH$_2$) 29.47 (CH$_2$×2), 29.36 (CH$_2$×2), 29.10 (CH$_2$×2), 29.02 (CH$_2$) 28.83 (CH$_2$), 28.67 (CH$_2$), 22.69 (CH$_2$), 14.11 (CH$_3$)

HRMS (ESI-TOF) m/z calcd for C$_{26}$H$_{50}$O$_3$S [M]$^+$ 442.3481, found 442.3495.

(2) Binding of Compound 13a to 13f to BGL Trimer

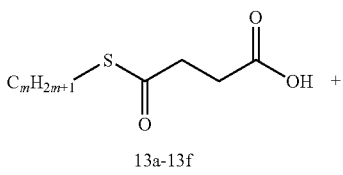

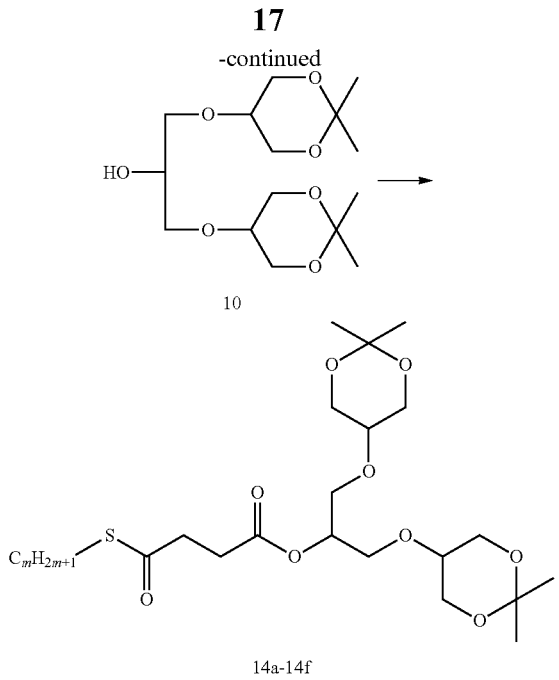

To a methylene chloride solution (3.310 mL, 13a to 13f concentration: 0.20 mol/L) containing 4-alkylthio-4-oxobutylic acid 13a to 13f (0.662 mmol, 1 eq), BGL trimer (Compound 10) (254.2 mg, 0.794 mmol, 1.20 eq) and 4-dimethylaminopyridine (DMAP) (8.0 mg, 0.066 mmol, 0.10 eq), 1-ethyl-3-(3-dimethylaminopropyl)carbodiimide hydrochloride salt (EDC.HCl) (152.30 mg, 0.794 mmol, 1.20 eq) were added at room temperature. The mixed solution was stirred at room temperature for 20 to 24 hours and then poured to 10% ammonium chloride aqueous solution (50 mL), and extraction was carried out two times using methylene chloride (50 mL). The obtained extract was washed two times using saturated sodium chloride aqueous solution (50 mL), dried using anhydrous sodium sulfate (3 g) and concentrated. Compound 14a to 14f were obtained by purification from the residue using a silica gel column (methylene chloride:acetone=95:5) (yield amount: 0.430 to 0.602 mmol, yield: 65 to 91%).

[14a]

FT-IR (neat): 2995, 2925, 855, 1740, 1692, 1461, 1372, 1251, 1227, 1199, 1155, 1086, 985 cm$^{-1}$ $^1$H NMR (CDCl$_3$, 400 MHz): δ5.08 (q, J=5.2 Hz, 1H), 3.95-4.00 (m, 4H), 3.63-3.77 (m, 8H), 3.44-3.50 (m, 2H), 2.90 (t, J=7.6 Hz, 4H), 2.69 (t, J=7.2 Hz, 2H), 1.58 (q, J=7.2 Hz, 2H), 1.45 (s, 6H), 1.42 (s, 6H), 1.28 (m, 22H), 0.90 (t, J=6.8 Hz, 3H)

$^{13}$C NMR (CDCl$_3$, 125 MHz): δ197.70 (C, S—C=O), 171.41 (C, CO$_2$) 98.18 (C×2, C (CH$_3$)$_2$), 71.95 (CH, OCH (CH$_2$)$_2$), 70.98 (CH×2, OCH (CH$_2$)$_2$), 67.04 (CH$_2$×2, OCH (CH$_2$)$_2$), 62.49 (CH$_2$×2, OCH (CH$_2$)$_2$) 62.37 (CH×2), 38.39 (CH$_2$), 31.88 (CH$_2$), 29.61 (CH$_2$) 29.59 (CH$_2$) 29.54 (CH$_2$), 29.48 (CH$_2$), 29.46 (CH$_2$) 29.30 (CH$_2$) 29.09 (CH$_2$×2), 28.94 (CH$_2$), 28.83 (CH$_2$), 24.22 and 22.92 (CH$_3$×4, C (CH$_3$)$_2$), 22.65 (CH$_2$), 14.09 (CH$_3$)

HRMS (ESI-TOF) m/z calcd for C$_{32}$H$_{56}$O$_9$S [M]$^+$ 604.3645, found 604.3652.

[14b]

FT-IR (neat): 2991, 2922, 2852, 1737, 1686, 1459, 1364, 1252, 1226, 1195, 1150, 1088, 980, 936, 828, 728 cm$^{-1}$ $^1$H NMR (CDCl$_3$, 400 MHz): δ5.08 (q, J=4.8 Hz, 1H), 3.95-4.00 (m, 4H), 3.63-3.77 (m, 8H), 3.45-3.50 (m, 2H), 2.90 (t, J=7.6 Hz, 4H), 2.69 (t, J=6.8 Hz, 2H), 1.58 (q, J=7.2 Hz, 2H), 1.45 (s, 6H), 1.42 (s, 6H), 1.28 (m, 22H), 0.90 (t, J=6.8 Hz, 3H)

$^{13}$C NMR (CDCl$_3$, 125 MHz): δ197.67 (C, S—C=O), 171.40 (C, CO$_2$) 98.17 (C×2, C (CH$_3$)$_2$), 71.96 (CH, OCH (CH$_2$)$_2$), 71.00 (CH×2, OCH (CH$_2$)$_2$), 67.05 (CH$_2$×2, OCH (CH$_2$)$_2$), 62.49 (CH$_2$×2, OCH (CH$_2$)$_2$) 62.37 (CH$_2$×2, OCH (CH$_2$)$_2$), 38.39 (CH$_2$), 31.89 (CH$_2$), 29.61 (CH$_2$×3), 29.54 (CH$_2$), 29.47 (CH$_2$), 29.46 (CH$_2$) 29.30 (CH$_2$×2), 29.09 (CH$_2$×2), 28.94 (CH$_2$), 28.82 (CH$_2$), 24.25 and 22.90 (CH$_3$×4, C (CH$_3$)$_2$), 22.65 (CH$_2$), 14.08 (CH$_3$)

HRMS (ESI-TOF) m/z calcd for C$_{33}$H$_{60}$O$_9$S [M]$^+$ 632.3958, found 632.3929.

[14c]

FT-IR (neat): 2995, 2926, 2850, 1744, 1688, 1462, 1367, 1248, 1223, 1192, 1154, 1092, 978, 940 cm$^{-1}$ $^1$H NMR (CDCl$_3$, 500 MHz): δ5.07 (quint, J=5 Hz, 1H, OCH (CH$_2$)$_2$), 3.98-3.94 (m, 4H, CHCH$_2$O), 3.75-3.71 (m, 4H, CHCH$_2$O), 3.69-3.62 (m, 4H, CHCH$_2$O) 3.48-3.44 (m, 2H, OCH (CH$_2$)$_2$), 2.90-2.87 (m, 4H, SCOCH$_2$ and CH$_2$SCO) 2.68 (t, J=7 Hz, 2H, CH$_2$CO$_2$) 1.57 (quint, J=7 Hz, 2H, CH$_2$CH$_2$S) 1.44 and 1.41 (s, 12H, CCH$_3$), 1.36-1.22 (m, 26H, alkylic CH$_2$) 0.89 (t, J=7 Hz, 3H, CH$_3$)

$^{13}$C NMR (CDCl$_3$, 125 MHz): δ197.72 (C, S—C=O), 171.43 (C, CO$_2$) 98.20 (C×2, C (CH$_3$)$_2$), 71.96 (CH, °CH (CH$_2$)$_2$), 70.99 (CH×2, OCH (CH$_2$)$_2$), 67.06 (CH$_2$×2, OCH (CH$_2$)$_2$), 62.51 (CH$_2$×2, OCH (CH$_2$)$_2$) 62.39 (CH$_2$×2, OCH (CH$_2$)$_2$), 38.40 (CH$_2$), 31.91 (CH$_2$), 29.67 (CH$_2$×3), 29.65 (CH$_2$), 29.63 (CH$_2$), 29.57 (CH$_2$) 29.48 (CH$_2$×2), 29.34 (CH$_2$) 29.30 (CH$_2$), 29.11 (CH$_2$), 28.96 (CH$_2$×2), 28.85 (CH$_2$), 24.25 and 22.92 (CH$_3$×4, C (CH$_3$)$_2$), 22.68 (CH$_2$), 14.10 (CH$_3$)

HRMS (ESI-TOF) m/z calcd for C$_{35}$H$_{64}$O$_9$SNa [M+Na]$^+$ 683.4169, found 683.4177.

[14d]

FT-IR (neat): 2918, 2850, 2360, 2341, 1737, 1692, 1469, 1372, 1251, 1200, 1086, 985, 938, 830, 721 cm$^{-1}$ $^1$H NMR (CDCl$_3$, 500 MHz): δ5.06 (quint, J=5 Hz, 1H, OCH (CH$_2$)$_2$), 3.96 (dd, J=4, 11.5 Hz, 2H, CHCH$_2$O), 3.95 (dd, J=3.5, 11.5 Hz, 2H, CHCH$_2$O), 3.729 (dd, J=6, 11.5 Hz, 2H, CHCH$_2$O), 3.723 (dd, J=6, 11.5 Hz, 2H, CHCH$_2$O), 3.67 (dd, J=5, 11.5 Hz, 2H, CHCH$_2$O), 3.63 (dd, J=5, 11.5 Hz, 2H, CHCH$_2$O) 3.47-3.43 (m, 2H, OCH (CH$_2$)$_2$), 2.881 (t, J=7 Hz, 2H, SCOCH$_2$), 2.876 (t, J=7.5 Hz, 2H, CH$_2$SCO), 2.67 (t, J=7 Hz, 2H, CH$_2$C°2), 1.55 (quint, J=7.5 Hz, 2H, CH$_2$CH$_2$S), 1.43 and 1.40 (s, 12H, CCH$_3$×4), 1.38-1.25 (m, 30H, alkylic CH$_2$), 0.88 (t, J=7 Hz, 3H, CH$_3$C$_{17}$H$_{34}$S)

$^{13}$C NMR (CDCl$_3$, 125 MHz): δ197.8 (C, —S—C=O), 171.5 (C, CO$_2$), 98.2 (C×2, C (CH$_3$)$_2$), 72.0 (CH, OCH (CH$_2$)$_2$), 71.0 (CH×2, OCH (CH$_2$)$_2$), 67.1 (CH$_2$×2, OCH (CH$_2$)$_2$), 62.5 (CH$_2$×2, OCH (CH$_2$)$_2$), 62.4 (CH$_2$×2, OCH (CH$_2$)$_2$), 38.4 (CH$_2$), 32.0 (CH$_2$), 29.72 (CH$_2$×5), 29.70 (CH$_2$×2), 29.64 (CH$_2$), 29.5 (CH$_2$×2), 29.4 (CH$_2$), 29.3 (CH$_2$), 29.2 (CH$_2$), 29.0 (CH$_2$×2), 24.3 and 23.0 (CH$_3$×4, C (CH)$_2$), 22.7 (CH$_2$), 14.2 (CH$_3$)

HRMS (ESI-TOF) m/z calcd for C$_{37}$H$_{68}$O$_9$SNa [M+Na]$^+$ 711.4482, found 711.4492.

[14e]

FT-IR (neat): 2991, 2922, 2852, 1737, 1686, 1459, 1371, 1245, 1195, 1156, 1088, 980, 936, 828, 753 cm$^{-1}$ $^1$H NMR (CDCl$_3$, 400 MHz): δ5.08 (quint, J=5.2 Hz, 1H, OCH (CH$_2$)$_2$), 3.99-3.95 (m, 4H, CHCH$_2$O), 3.76-3.72 (m, 4H, CHCH$_2$O), 3.71-3.63 (m, 4H, CHCH$_2$O), 3.50-3.44 (m, 2H, OCH (CH$_2$) 2), 2.90 (t, J=7.6 Hz, 4H, SCOCH$_2$ and CH$_2$SCO), 2.69 (t, J=6.8 Hz, 2H, CH$_2$CO$_2$), 1.58 (quint, J=6.8 Hz, 2H, CH$_2$CH$_2$S), 1.45 and 1.42 (s, 12H, CCH$_3$×4), 1.38-1.28 (m, 34H, alkylic CH$_2$×17), 0.90 (t, J=7.2 Hz, 3H, CH$_3$)

$^{13}$C NMR (CDCl$_3$, 125 MHz): δ197.67 (C, S—C=O), 171.41 (C, CO$_2$H), 98.17 (C×2, C (CH$_3$)$_2$), 71.95 (CH, OCH (CH$_2$)$_2$), 70.98 (CH×2, OCH (CH$_2$)$_2$), 67.04 (CH$_2$×2, OCH (CH$_2$)$_2$), 62.49 (CH$_2$×2, OCH (CH$_2$)$_2$), 62.37 (CH$_2$×2, OCH (CH$_2$)$_2$), 38.39 (CH$_2$), 31.90 (CH$_2$), 29.67 (CH$_2$×7), 29.63 (CH$_2$×2), 29.56 (CH$_2$), 29.48 (CH$_2$×2), 29.34 (CH$_2$), 29.29 (CH$_2$), 29.10 (CH$_2$), 28.94 (CH$_2$×2), 28.84 (CH$_2$), 24.23 and 22.92 (CH$_3$×4, C (CH$_3$)$_2$), 22.67 (CH$_2$), 14.10 (CH$_3$)

HRMS (ESI-TOF) m/z calcd for C$_{39}$H$_{72}$O$_9$S [M]$^+$ 716.4897, found 716.4899.

[14f]

FT-IR (neat): 2991, 2922, 2859, 1737, 1686, 1466, 1377, 1245, 1195, 1150, 1093, 1037, 980, 936, 828, 753, 728 cm$^{-1}$ $^1$H NMR (CDCl$_3$, 500 MHz): δ5.05 (quint, J=5 Hz, 1H, OCH (CH$_2$)$_2$), 3.96-3.92 (m, 4H, CHCH$_2$O), 3.73-3.69 (m, 4H, CHCH$_2$O), 3.68-3.61 (m, 4H, CHCH$_2$O), 3.46-3.42 (m, 2H, OCH (CH$_2$)$_2$), 2.88-2.85 (m, 4H, SCOCH$_2$ and CH$_2$SCO), 2.66 (t, J=7 Hz, 2H, CH$_2$CO$_2$) 1.55 (quint, J=7 Hz, 2H, CH$_2$CH$_2$S), 1.42 and 1.38 (s, 12H, CCH$_3$), 1.35-1.18 (m, 38H, alkylic CH$_2$), 0.87 (t, J=7 Hz, 3H, CH$_3$)

$^{13}$C NMR (CDCl$_3$, 125 MHz): δ197.65 (C, S—C=O), 171.39 (C, CO$_2$), 98.15 (C×2, C (CH$_3$)$_2$), 71.95 (CH, OCH (CH$_2$)$_2$), 70.98 (CH×2, OCH (CH$_2$)$_2$), 67.04 (CH$_2$×2, OCH (CH$_2$)$_2$) 62.48 (CH$_2$×2, OCH (CH$_2$)$_2$) 62.36 (CH$_2$×2, OCH (CH$_2$)$_2$), 38.38 (CH$_2$), 31.90 (CH$_2$), 29.67 (CH$_2$×8) 29.64 (CH$_2$), 29.62 (CH$_2$×2) 29.56 (CH$_2$), 29.49 (CH$_2$), 29.47 (CH$_2$) 29.33 (CH$_2$×2), 29.28 (CH$_2$), 29.10 (CH$_2$), 28.93 (CH$_2$), 28.83 (CH$_2$) 24.23 and 22.90 (CH$_3$×4, C (CH$_3$)$_2$), 22.66 (CH$_2$), 14.08 (CH$_3$)

HRMS (ESI-TOF) m/z calcd for C$_{41}$H$_{77}$O$_9$S [M+H]$^+$ 745.5288, found 745.5281.

(3) Deprotection of Compound 14a to 14f 14a-14f 15a-15f

To a 0.10 mol/L methanol solution (5.37 mL) of Compound 14a to 14f (0.537 mmol, 1.0 eq), an ion-exchange resin ("Amberlyst® 17" manufactured by Rohm and Haas) (100 mg) was added at room temperature. The obtained suspension was stirred at room temperature for 2 to 5 hours. The ion-exchange resin was removed by filtration, and the obtained filtrate was concentrated to obtain colorless and gum like hydrophilic metal surface treatment agent 15a to 15f (yield amount: 0.446 to 0.526 mmol, yield: 83 to 98%).

[15a]

FT-IR (neat): 3401, 3010, 2928, 2852, 1737, 1680, 1459, 1409, 1377, 1220, 1170, 1119, 1068, 1043, 986 cm$^{-1}$ $^1$H NMR (CDCl$_3$, 500 MHz): δ5.13 (q, J=5.2 Hz, 1H), 3.81 (ddd, J=5.6 Hz, 4H), 3.58-3.68 (m, 8H), 3.45 (q, J=5.2 Hz, 2H), 2.90-2.94 (m, 4H), 2.69 (t, J=5.6 Hz, 2H), 1.59 (q, J=7.2 Hz, 2H), 1.32 (s, br, 22H), 0.92 (t, J=6.8 Hz, 3H)

$^{13}$C NMR (CDCl$_3$, 125 MHz): δ198.35 (C, S—C=O), 172.06 (C, CO$_2$), 81.79 (CH×2, OCH (CH$_2$)$_2$), 72.67 (CH, OCH (CH$_2$)$_2$), 68.26 (CH$_2$×2, OCH (CH$_2$)$_2$), 61.11 (CH$_2$×2, OCH (CH$_2$)$_2$), 61.07 (CH$_2$×2, OCH (CH$_2$)$_2$) 37.95 (CH$_2$), 31.67 (CH$_2$), 29.38 (CH$_2$) 29.36 (CH$_2$) 29.29 (CH$_2$) 29.22 (CH$_2$×2), 29.07 (CH$_2$), 28.86 (CH$_2$), 28.83 (CH$_2$), 28.43 (CH$_2$) 28.27 (CH$_2$), 22.34 (CH$_2$), 13.06 (CH$_3$)

HRMS (ESI-TOF) m/z calcd for C$_{25}$H$_{48}$O$_9$S [M]$^+$ 524.3019, found 524.3051.

[15b]

FT-IR (neat): 3411, 2974, 2923, 2859, 1738, 1686, 1465, 1408, 1211, 1174, 1122, 1072, 755 cm$^{-1}$ $^1$H NMR (CDCl$_3$, 400 MHz): δ5.12 (q, J=5.2 Hz, 1H) 3.81 (ddd, J=5.6 Hz, 4H), 3.57-3.68 (m, 8H), 3.45 (q, J=5.2 Hz, 2H), 2.89-2.94 (m, 4H), 2.69 (t, J=6.8 Hz, 2H), 1.58 (q, J=7.2 Hz, 2H), 1.31 (s, br, 22H), 0.92 (t, J=6.8 Hz, 3H)

$^{13}$C NMR (CDCl$_3$, 125 MHz): δ198.30 (C, S—C=O), 172.03 (C, CO$_2$) 81.79 (CH×2, OCH (CH$_2$)), 72.67 (CH, OCH (CH$_2$) 2), 68.26 (CH$_2$×2, OCH (CH$_2$)$_2$), 61.13 (CH$_2$×2, OCH (CH$_2$)$_2$), 61.09 (CH$_2$×2, OCH (CH$_2$)$_2$) 37.97 (CH$_2$), 31.69 (CH$_2$), 29.44 (CH$_2$) 29.41 (CH$_2$) 29.39 (CH$_2$×2), 29.32 (CH$_2$), 29.25 (CH$_2$), 29.10 (CH$_2$) 28.86 (CH$_2$) 28.61 (CH$_2$) 28.47 (CH$_2$), 28.45 (CH$_2$), 28.29 (CH$_2$), 22.36 (CH$_2$), 13.11 (CH$_3$) HRMS (ESI-TOF) m/z calcd for C$_{271-15309}$S [M+H]$^+$ 553.3410, found 553.3438.

[15c]

FT-IR (neat): 3401, 2960, 2922, 2852, 1737, 1692, 1466, 1409, 1339, 1207, 1131, 1088, 1062 cm$^{-1}$ $^1$H NMR (CDCl$_3$, 400 MHz): δ5.13 (q, J=5 Hz, 1H) 3.81 (ddd, J=5.5 Hz, 4H), 3.67-3.58 (m, 8H), 3.45 (q, J=5 Hz, 2H), 2.94-2.90 (m, 4H), 2.70 (t, J=7 Hz, 2H), 1.59 (q, J=7.5 Hz, 2H), 1.40-1.31 (m, 26H), 0.92 (t, J=7 Hz, 3H)

$^{13}$C NMR (CDCl$_3$, 125 MHz): δ198.20 (C, S—C=O), 172.01 (C, CO$_2$) 81.78 (CH×2, OCH (CH$_2$)$_2$), 72.66 (CH, OCH (CH$_2$)$_2$), 68.26 (CH$_2$×2, OCH (CH$_2$)$_2$), 61.15 (CH$_2$×2, OCH (CH$_2$)$_2$), 61.11 (CH$_2$×2, OCH (CH$_2$)$_2$), 38.02 (CH$_2$), 31.75 (CH$_2$), 29.49 (CH$_2$×3), 29.45 (CH$_2$×2), 29.43 (CH$_2$), 29.40 (CH$_2$), 29.32 (CH$_2$), 29.17 (CH$_2$), 28.93 (CH$_2$), 28.88 (CH$_2$×2), 28.56 (CH$_2$), 28.35 (CH$_2$), 22.42 (CH$_2$), 13.22 (CH$_3$)

HRMS (ESI-TOF) m/z calcd for C$_{291-15709}$S [M+H]$^+$ 581.3723, found 581.3704.

[15d]

FT-IR (KBr): 3403, 2918, 2850, 2360, 2342, 1734, 1686, 1468, 1127, 1073, 474, 448, 421, 411 cm$^{-1}$ $^1$H NMR (CDCl$_3$, 500 MHz): δ5.14 (quint, J=5 Hz, 1H, OCH (CH$_2$)$_2$), 3.87-3.82 (m, 4H, CHCH$_2$O), 3.79-3.73 (m, 4H, CHCH$_2$O), 3.71-3.64 (m, 4H, CHCH$_2$O), 3.67 (dd, J=5.0, 11.5 Hz, 2H, CHCH$_2$O), 3.63 (dd, J=5, 11.5 Hz, 2H, CHCH$_2$O), 3.55-3.51 (m, 2H, OCH (CH$_2$)$_2$), 2.99 (brs, 2H, CH$_2$OH), 2.98 (t, J=6.5 Hz, 2H, SCOCH$_2$), 2.88 (t, J=7.5 Hz, 2H, CH$_2$SCO), 2.93-2.86 (brs(hidden), 2H, CH$_2$OH), 2.67 (t, J=7 Hz, 2H, CH$_2$CO$_2$), 1.56 (quint, J=8 Hz, 2H, CH$_2$CH$_2$S), 1.34-1.20 (m, 30H, alkylic CH$_2$), 0.88 (t, J=7 Hz, 3H, CH$_3$C$_{17}$H$_{34}$S)

$^{13}$C NMR (CDCl$_3$, 125 MHz): δ198.6 (C, S—C=O), 171.8 (C, CO$_2$), 81.2 (CH×2, OCH (CH$_2$)$_2$), 72.0 (CH, OCH (CH$_2$)$_2$), 68.1 (CH$_2$×2, OCH (CH$_2$)$_2$), 62.4 (CH$_2$×2, OCH (CH$_2$)$_2$), 62.2 (CH$_2$×2, OCH (CH$_2$)$_2$), 38.4 (CH$_2$), 32.0 (CH$_2$), 29.76 (CH$_2$×5), 29.71 (CH$_2$×3), 29.65 (CH$_2$) 29.55 (CH$_2$), 29.44 (CH$_2$), 29.42 (CH$_2$), 29.3 (CH$_2$), 29.2 (CH$_2$), 28.9 (CH$_2$), 22.8 (CH$_2$), 14.2 (CH$_3$)

HRMS (ESI-TOF) m/z calcd for C$_{31}$H$_{60}$O$_9$SNa [M+Na]$^+$ 631.3856, found 631.3913.

[15e]

FT-IR (neat): 3403, 3020, 2920, 2857, 1739, 1688, 1462, 1417, 1380, 1210, 1122, 1066, 777, 745, 664 cm$^{-1}$ $^1$H NMR (CDCl$_3$, 400 MHz): δ5.17 (quint, J=5.2 Hz, 1H, OCH (CH$_2$)$_2$), 3.87 (d, J=4.8 Hz, 4H, CHCH$_2$O), 3.83-3.76 (m, 4H, CHCH$_2$O), 3.73-3.67 (m, 4H, CHCH$_2$O), 3.58-3.53 (m, 2H, OCH (CH$_2$)$_2$), 2.95-2.89 (m, 4H, SCOCH$_2$ and CH$_2$SCO) 2.71-2.67 (m, 2H, CH$_2$CO$_2$) 1.58 (quint, J=7 Hz, 2H, CH$_2$CH$_2$S), 1.38-1.28 (m, 34H, alkylic CH$_2$), 0.90 (t, J=7 Hz, 3H, CH$_3$)

$^{13}$C NMR (CDCl$_3$, 125 MHz): δ198.45 (C, S—C=O), 171.82 (C, CO$_2$) 81.28 (CH×2, OCH (CH$_2$)$_2$), 72.10 (CH, OCH (CH$_2$)$_2$), 68.04 (CH$_2$×2, OCH (CH$_2$)$_2$), 62.07 (CH$_2$×2, OCH (CH$_2$)$_2$), 61.95 (CH$_2$×2, OCH (CH$_2$)$_2$) 38.35 (CH$_2$) 31.91 (CH$_2$), 29.69 (CH$_2$×7), 29.65 (CH$_2$×2) 29.60 (CH$_2$) 29.51 (CH$_2$), 29.40 (CH$_2$), 29.53 (CH$_2$) 29.26 (CH$_2$×2) 29.14 (CH$_2$), 29.04 (CH$_2$), 28.86 (CH$_2$), 22.68 (CH$_2$), 14.11 (CH$_3$)

HRMS (ESI-TOF) m/z calcd for C$_{33}$H$_{64}$O$_9$S [M]$^+$ 636.4271, found 636.4233.

[15f]

FT-IR (neat): 3408, 3016, 2916, 2846, 1737, 1692, 1471, 1409, 1377, 1213, 1131, 1068, 974, 760 cm$^{-1}$ $^1$H NMR (CDCl$_3$, 500 MHz): δ5.14 (quint, J=5 Hz, 1H, OCH (CH$_2$)$_2$), 3.89-3.83 (m, 4H, CHCH$_2$O), 3.81-3.76 (m, 4H, CHCH$_2$O), 3.72-3.67 (m, 4H, CHCH$_2$O) 3.56-3.53 (m, 2H, OCH (CH$_2$) 2), 3.29-2.73 (brs (hidden), 4H, CH$_2$OH), 2.95-2.89 (m, 4H, SCOCH$_2$ and CH$_2$SCO), 2.69 (t, J=7.5 Hz, 2H, CH$_2$CO$_2$) 1.58 (quint, J=7 Hz, 2H, CH$_2$CH$_2$S) 1.38-1.24 (m, 38H, alkylic CH$_2$) 0.90 (t, J=7 Hz, 3H, CH$_3$)

$^{13}$C NMR (CDCl$_3$, 125 MHz): δ198.49 (C, COS), 171.71 (C, CO$_2$), 81.23 (CH×2, OCH (CH$_2$)$_2$), 71.98 (CH, OCH (CH$_2$)$_2$), 68.12 (CH$_2$×2, OCH (CH$_2$)$_2$), 62.37 (CH$_2$×2, OCH (CH$_2$)$_2$), 62.21 (CH$_2$×2, OCH (CH$_2$)$_2$), 38.35 (CH$_2$), 31.92 (CH$_2$), 29.70 (CH$_2$×5), 29.65 (CH$_2$×3), 29.59 (CH$_2$×2), 29.50 (CH$_2$), 29.40 (CH$_2$), 29.35 (CH$_2$×2), 29.27 (CH$_2$×2), 29.13 (CH$_2$), 29.06 (CH$_2$×2), 28.85 (CH$_2$), 22.69 (CH$_2$) 14.11 (CH$_3$)

HRMS (ESI-TOF) m/z calcd for C$_{35}$H$_{69}$O$_9$S [M+H]$^+$ 665.4662, found 665.4633.

Example 3: Production of Hydrophilic Metal Surface Treatment Agent (1) Synthesis of Dibromo Compound

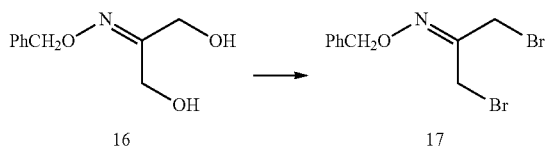

A stirred methylene chloride solution (51 mL) of Compound 16 (5.0 g, 25.6 mmol) (Reference: Ludovic Merckl et al., Chem. Bio. Chem., 2005, 6, 1866-1874) was cooled using an ice bath for 25 minutes. Carbon tetrabromide (18.68 g, 56.3 mmol) and triphenylphosphine (14.8 g, 56.3 mmol) were added to the stirred solution at 0° C. The obtained mixture was stirred at room temperature for 9 hours. The obtained suspension was subjected to filtration, and the filtrate was concentrated under reduced pressure. The obtained residue was subjected to silica gel column chromatography (eluent: hexane/methylene chloride=2/1) to obtain the target Compound 17 (yield amount: 6.51 g, 20.3 mmol, yield: 79%).

FT-IR (neat): 3032, 2936, 2882, 1607, 1497, 1454, 1426, 1367, 1206, 1141, 1081, 1017, 911, 846, 828, 736, 698, 627, 569 cm$^{-1}$ $^1$H NMR (CDCl$_3$, 500 MHz): δ7.36-7.33 (m, 5H, aromatic), 5.19 (s, 2H, Ph-CH$_2$—O), 4.18 (s, 2H, C—CH$_2$—Br), 4.15 (s, 2H, C—CH$_2$—Br)

$^{13}$C NMR (CDCl$_3$, 125 MHz): δ151.6 (C, C=N), 136.9 (C, aromatic), 128.6 (CH×2, aromatic), 128.3 (CH, aromatic), 128.2 (CH×2, aromatic), 77.0 (CH$_2$, Ph-CH$_2$—O), 29.7 (CH$_2$, C—CH$_2$—Br), 18.6 (CH$_2$, C—CH$_2$—Br)

HRMS (ESI-TOF) m/z calcd for C$_{10}$H$_{11}$NOBr$_2$Na [M+Na]$^+$ 341.9105 found 341.9121.

(2) Condensation with BGL trimer

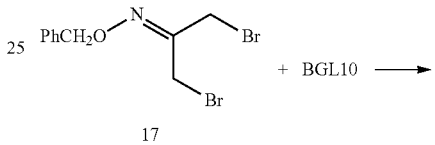

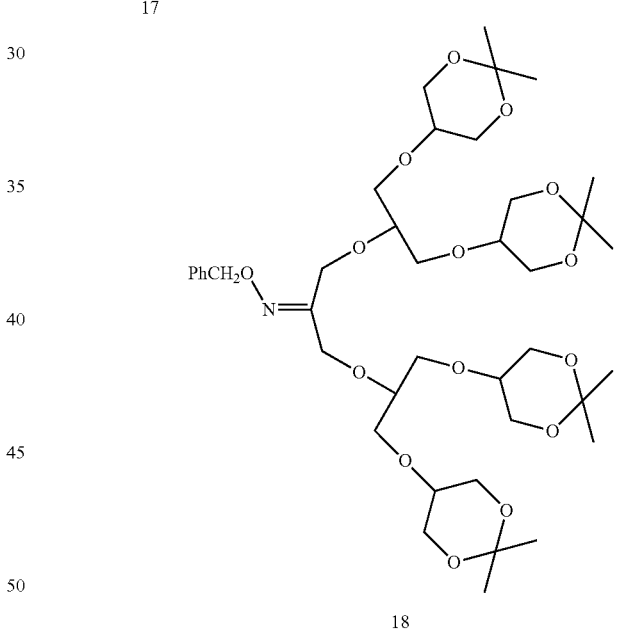

Sodium hydride (55% in mineral oil, 0.85 g, 19.62 mmol) was added to a stirred 1,4-dioxane solution (13.0 mL) of Compound (2.10 g, 6.54 mmol) and BGL trimer 10 (4.6 g, 14.38 mmol) at room temperature over 10 minutes. After an evolution of hydrogen gas died down, the mixture was stirred at 45° C. for 18 hours. The obtained mixture was poured into a saturated sodium chloride aqueous solution, and extraction was repeated two times using ethyl acetate (50 mL). The obtained organic phase was dried using anhydrous sodium sulfate and concentrated under reduced pressure. The residue was subjected to silica gel column chromatography (eluent:methylene chloride/acetone=3/1) to obtain the target Compound 18 (yield amount: 3.30 g, 4.16 mmol, yield: 63%).

FT-IR (neat): 2992, 2873, 2306, 2247, 1455, 1372, 1251, 1288, 1199, 1094, 1043, 937, 830, 733, 700 cm$^{-1}$ $^1$H NMR (CDCl$_3$, 500 MHz): δ7.37-7.30 (m, 5H, aromatic), 5.09 (s, 2H, Ph-CH$_2$—ON), 4.47 (s, 2H, C—CH$_2$—O), 4.25 (s, 2H, C—CH$_2$—O), 3.95-3.90 (m, 8H, CH—CH$_2$—O), 3.72-3.67 (m, 8H, CH—CH$_2$—O), 3.64-3.60 (m, 2H, O—CH—CH$_2$), 3.58-3.50 (m, 8H, CH—CH$_2$—O), 3.44-3.39 (m, 4H, O—CH—CH$_2$), 1.42, 1.41 and 1.39 (s, 24H, C—CH$_3$)

$^{13}$C NMR (CDCl$_3$, 125 MHz): δ156.6 (C, C=N), 137.5 (C, aromatic), 128.4 (CH×2, aromatic), 128.2 (CH×2, aromatic), 128.0 (CH, aromatic), 98.2 (C×4, O—C—O), 78.6 (CH, O—CH—CH$_2$), 77.3 (CH, O—CH—CH$_2$) 76.3 (CH$_2$, Ph-CH$_2$—O), 71.01 (CH×2, O—CH(—CH$_2$)$_2$), 70.98 (CH×2, O—CH (CH$_2$)$_2$), 68.4 (CH$_2$, C—CH$_2$—O) 68.3 (CH$_2$, C—CH$_2$—O) 67.7 (CH$_2$×2, CH—CH$_2$—O), 62.7 (CH$_2$×2, CH—CH$_2$—O), 62.60 (CH$_2$×2, CH—CH$_2$—O), 62.58 (CH$_2$×2, CH—CH$_2$—O), 62.55 (CH$_2$×2, CH—CH$_2$—O), 62.53 (CH$_2$×2, CH—CH$_2$—O), 24.7 (CH$_3$×2, C—CH$_3$), 24.5 (CH$_3$×2, C—CH$_3$), 22.8 (CH$_3$×2, C—CH$_3$) 22.6 (CH$_3$×2, C—CH$_3$)

HRMS (ESI-TOF) m/z calcd for C$_{40}$H$_{65}$NO$_{15}$Na [M+Na]$^+$ 822.4260 found 822.4252.

(3) Reduction of Imino Group

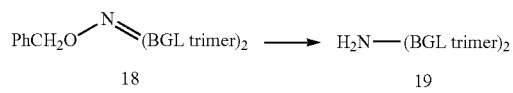

Compound 18 (0.1 g, 0.125 mmol) was dissolved in distilled methanol (10 mL). Ammonium formate (0.039 mg, 0.625 mmol) and formic acid (24 μL, 0.625 mmol) were sequentially added to the solution, and the mixture was stirred at room temperature for 1 hour. Palladium/activated carbon (10% Pd, 50 mg) was added thereto, and the obtained suspension was stirred at 45° C. for 24 hours. Saturated sodium hydrogencarbonate aqueous solution (50 mL) was added to the suspension, and extraction was repeated two times using methylene chloride (100 mL). The obtained extract was dried using potassium carbonate and concentrated under reduced pressure. The residue was subjected to silica gel column chromatography (eluent: methylene chloride/methanol=5/1) to obtain the target Compound 19 (yield amount: 0.04 g, 0.0574 mmol, yield: 46%).

FT-IR (neat): 2992, 2873, 2306, 2247, 1455, 1372, 1251, 1288, 1199, 1094, 1043, 937, 830, 733, 700 cm$^{-1}$ $^1$H NMR (CDCl$_3$, 500 MHz): δ7.37-7.30 (m, 5H, aromatic), 5.09 (s, 2H, Ph-CH$_2$—ON), 4.47 (s, 2H, C—CH$_2$—O), 4.25 (s, 2H, C—CH$_2$—O), 3.95-3.90 (m, 8H, CH—CH$_2$—O), 3.72-3.67 (m, 8H, CH—CH$_2$—O), 3.64-3.60 (m, 2H, O—CH—CH$_2$), 3.58-3.50 (m, 8H, CH—CH$_2$—O), 3.44-3.39 (m, 4H, O—CH—CH$_2$), 1.42, 1.41 and 1.39 (s, 24H, C—CH$_3$)

$^{13}$C NMR (CDCl$_3$, 125 MHz): δ156.6 (C, C=N), 137.5 (C, aromatic), 128.4 (CH×2, aromatic), 128.2 (CH×2, aromatic), 128.0 (CH, aromatic), 98.2 (C×4, O—C—O), 78.6 (CH, O—CH—CH$_2$), 77.3 (CH, O—CH—CH$_2$), 76.3 (CH$_2$, Ph-CH$_2$—O), 71.01 (CH×2, O—CH (CH$_2$)$_2$), 70.98 (CH×2, O—CH (CH$_2$)$_2$), 68.4 (CH$_2$, C—CH$_2$—O) 68.3 (CH$_2$, C—CH$_2$—O) 67.7 (CH$_2$×2, CH—CH$_2$—O), 62.7 (CH$_2$×2, CH—CH$_2$—O), 62.60 (CH$_2$×2, CH—CH$_2$—O), 62.58 (CH$_2$×2, CH—CH$_2$—O), 62.55 (CH$_2$×2, CH—CH$_2$—O), 62.53 (CH$_2$×2, CH—CH$_2$—O), 24.7 (CH$_3$×2, C—CH$_3$), 24.5 (CH$_3$×2, C—CH$_3$), 22.8 (CH$_3$×2, C—CH$_3$) 22.6 (CH$_3$×2, C—CH$_3$)

HRMS (ESI-TOF) m/z calcd for C$_{40}$H$_{65}$NO$_{15}$Na [M+Na]$^+$ 822.4260 found 822.4252.

(4) Condensation with Long Chain Hydrocarbon Compound

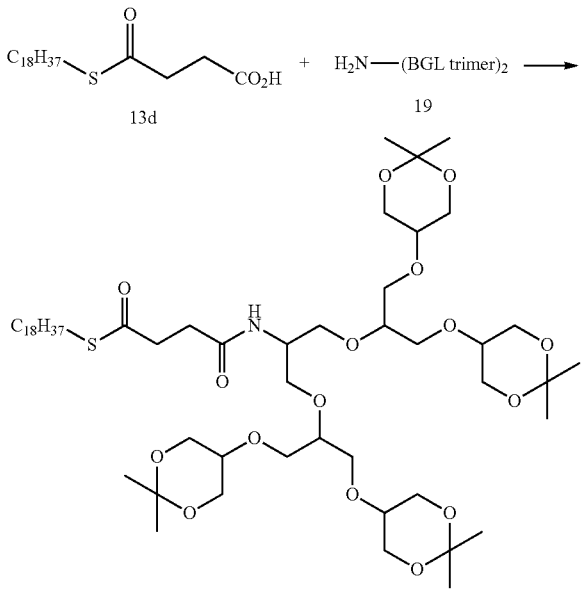

Compound 19 (459.3 mg, 0.66 mmol), N,N-dimethylaminopyridine (7.3 mg, 0.06 mmol) and 1-ethyl-3-(3-dimethylaminopropyl)carbodiimide hydrochloride (164.5 mg, 0.86 mmol) were added to a methylene chloride solution (5 mL) of 4-octadecylthio-4-oxobutanoic acid (Compound 13d) (309.5 mg, 0.8 mmol), and the obtained mixed solution was stirred at room temperature for 12 hours. The obtained mixture was poured to 1% KHSO$_4$ aqueous solution (15 mL), and extraction was repeated three times using methylene chloride (20 mL). The obtained extracts were collected, washed using saturated sodium chloride aqueous solution (30 mL), dried using anhydrous sodium sulfate and concentrated under reduced pressure. The residue was subjected to silica gel column chromatography (eluent: methylene chloride/acetone=5/1) to obtain Compound 20 as a colorless and transparent liquid (yield amount: 210.0 mg, 0.20 mmol, yield: 25%).

FT-IR (neat): 3336, 2925, 2854, 1679, 1533, 1467, 1372, 1251, 1228, 1199, 1096, 985, 940, 831, 732 cm$^{-1}$ $^1$H NMR (CDCl$_3$, 500 MHz): δ4.13 (quint, J=3.5 Hz, 1H, NCH (CH$_2$)$_2$), 3.98-3.93 (m, 6H, 4H of CHCH$_2$O and 2H of CHCH$_2$O), 3.76-3.70 (m, 8H, CHCH$_2$O), 3.62-3.50 (m, 12H, CHCH$_2$O), 3.43-3.40 (m, 4H, OCH (CH$_2$)$_2$), 2.89 (t, J=7 Hz, 2H, CH$_2$C$_0$) 2.86 (t, J=7.5 Hz, 2H, CH$_2$SCO), 2.54 (t, J=7 Hz, 2H, CH$_2$CO) 1.55 (quint, J=7.5 Hz, 2H, CH$_2$CH$_2$S), 1.42, 1.41 and 1.40 (s, 24H, CCH$_3$), 1.35-1.25 (m, 30H, alkylic CH$_2$) 0.88 (t, J=7 Hz, 3H, CH$_3$C$_{17}$H$_{34}$S)

$^{13}$C NMR (CDCl$_3$, 125 MHz): δ198.5 (C, S—C=O), 170.9 (C, CONH), 98.24 and 98.22 (C×4, C (CH$_3$) 2), 78.8 (CH×2, OCH (CH$_2$)$_2$) 71.2 (CH×2, OCH (CH$_2$)$_2$) 71.1 (CH×2, OCH (CH$_2$)$_2$), 68.9, 68.7, 62.6, 62.41, 62.36 (CH$_2$×14, CH (CH$_2$)$_2$) 49.5 (CH, NCH (CH$_2$)$_2$) 39.1 (CH$_2$) 31.9 (CH$_2$), 30.9 (CH$_2$), 29.71 (CH$_2$×5), 29.70 (CH$_2$), 29.64 (CH$_2$×2) 29.6 (CH$_2$), 29.5 (CH$_2$×2), 29.4 (CH$_2$), 29.2 (CH$_2$), 28.9 (CH$_2$×2), 24.0, 23.7, 23.6 and 23.0 (CH$_3$×8, C (CH$_3$)$_2$), 22.7 (CH$_2$), 14.1 (CH$_3$)

HRMS (ESI-TOF) m/z calcd for $C_{55}H_{101}NO_{16}SNa$ [M+Na]$^+$ 1086.6739, found 1086.6738.

(5) Deprotection

Compound 20 →

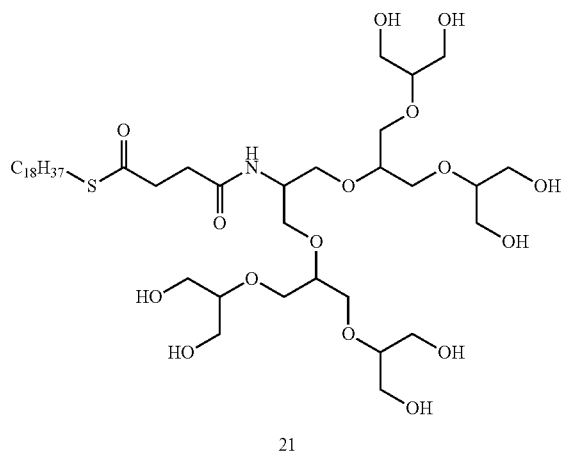

21

Ion-exchange resin ("Amberlyst® 15" manufactured by Rohm and Haas) (19.8 mg) was added to a methanol solution (2 mL) of Compound 20 (210.0 mg, 0.20 mmol). The obtained suspension was stirred at room temperature for 15 hours. The suspension was filtered, and the filtrate was concentrated under reduced pressure to obtain the target Compound 21 as a colorless amorphous compound (yield amount: 168.3 mg, 0.186 mmol, yield: 93%).

FT-IR (KBr): 3735, 3649, 3417, 2919, 2850, 2360, 234, 1653, 1558, 1541, 1457, 1121, 1074, 668 cm$^{-1}$ $^1$H NMR (CD$_3$OD, 500 MHz): δ4.11 (quint, J=5 Hz, 1H, NCH(CH$_2$)$_2$), 3.79-3.67 (m, 30H, 28H of CHCH$_2$O and 2H of OCH (CH$_2$)$_2$), 3.43 (quint, J=5 Hz, 4H, OCH (CH$_2$)$_2$), 2.88 (t, J=7 Hz, 2H, SCOCH$_2$), 2.87 (t, J=7 Hz, 2H, CH$_2$SCO), 2.55 (t, J=7 Hz, 2H, CH$_2$CONH), 1.56 (quint, J=7.5 Hz, 2H, CH$_2$CH$_2$S), 1.40-1.29 (m, 30H, alkylic CH$_2$), 0.90 (t, J=7 Hz, 3H, CH$_3$C$_{17}$H$_{34}$S)

$^{13}$C NMR (CD$_3$OD, 125 MHz): δ199.8 (C, S—C=O), 173.9 (C, CO$_2$), 83.2 (CH×4, OCH (CH$_2$)$_2$), 83.1 (CH×2, OCH (CH$_2$)$_2$), 80.4 (CH, NCH(CH$_2$)$_2$), 70.8 (CH$_2$×2, NCH (CH$_2$)$_2$), 69.9 (CH$_2$×4, OCH (CH$_2$)$_2$), 62.6 (CH$_2$×4, OCH (CH$_2$)$_2$), 62.5 (CH$_2$×4, OCH (CH$_2$)$_2$), 40.0 (CH$_2$) 33.1 (CH$_2$) 31.8 (CH$_2$) 30.78 (CH$_2$×2), 30.77 (CH$_2$×5), 30.75 (CH$_2$×2), 30.70 (CH$_2$), 30.6 (CH$_2$), 30.5 (CH$_2$) 30.3 (CH$_2$) 29.9 (CH$_2$) 29.7 (CH$_2$), 23.7 (CH$_2$), 14.4 (CH$_3$)

HRMS (ESI-TOF) m/z calcd for $C_{43}H_{85}O_{16}SNa$[M+Na]$^+$ 926.5487, found 926.5487.

Example 4: Production of BGL Thiol

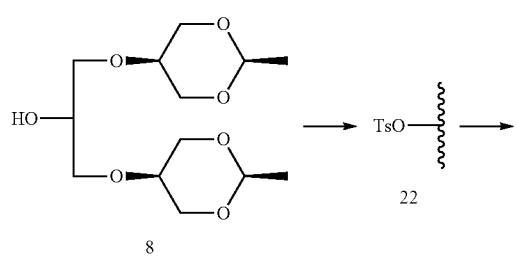

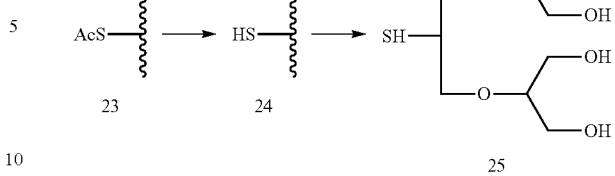

(1) Tosylation

A pyridine solution (20 mL, 19.74 mg, 24.9 mmol) of BGL trimer 8 (2.92 g, 10 mmol) and N,N-dimethyl-4-aminopyridine (122 mg, 1 mmol, 0.1 eq) was stirred at 0° C. To the obtained solution, p-toluenesulfonyl chloride (4.19 g, 22 mmol, 2.2 eq) was added under argon atmosphere over 2 minutes to be reacted at room temperature for 7 hours. The obtained liquid mixture was added to 5% copper sulfate aqueous solution (40 mL), and the mixture was subjected to extraction three times using ethyl acetate (60 mL). The obtained extract was washed three times using sodium hydrogencarbonate aqueous solution (40 mL), dried using anhydrous magnesium sulfate and concentrated to obtain the target Compound 22 (yield amount: 4.07 g, 0.91 mmol, yield: 91%) as a faint yellow oil. The obtained Compound 22 was not further purified and used in the next reaction.

$^1$H NMR (CDCl$_3$, 400 MHz): δ7.83 (d, J=8.0 Hz, 2H), 7.33 (d, J=8.0 Hz, 2H), 4.74 (quin, J=4.9 Hz, 1H), 4.67 (q, J=4.8 Hz, 2H), 4.10-3.99 (m, 4H), 3.82-3.71 (m, 8H), 3.24 (t, J=1.4 Hz, 2H, methyne×2), 2.44 (s, 3H), 1.31 (d, J=4.8 Hz, 6H)

$^{13}$C NMR (CDCl$_3$, 400 MHz): δ145.12 (C), 133.97 (C), 130.12 (CH×2), 128.36 (CH×2), 99.45 (CH×2), 80.09 (CH), 71.84 (CH×2), 69.03 (CH$_2$×2), 68.27 (CH$_2$×2), 67.19 (CH$_2$× 2), 21.99 (CH$_3$), 21.36 (CH$_3$×2)

(2) Synthesis of Thioacetate

An acetonitrile solution (186 mL, 146.01 g, 3.55 mol) of Compound 22 (41.55 g, 93.05 mmol) and potassium thioacetate (15.94 g, 139.57 mmol) was stirred under argon atmosphere at 80° C. for 8 hours. The obtained orange-colored turbid liquid mixture was subjected to filtration and washing using ethyl acetate. The obtained red mixed solution was concentrated, and the residue was subjected to short column chromatography (eluent: ethyl acetate) to obtain a red oily compound (31.5 g). Then, column chromatography (eluent:ethyl acetate/hexane=3/1) was conducted to obtain the target Compound 23 as a red oil (yield amount: 25.4 g, 72.48 mmol, yield: 78%).

$^1$H NMR (CDCl$_3$, 400 MHz): δ4.70 (q, J=5.1 Hz, 2H), 4.20-4.10 (m, 4H), 3.98-3.90 (m, 1H), 3.85-3.78 (m, 6H), 3.71 (dd, J=10.0 and 6.8 Hz, 2H), 3.27 (t, J=1.6 Hz, 2H), 2.33 (s, 3H), 1.33 (d, J=5.1 Hz, 6H)

(3) Thiolation

A methanol solution (68 mL, 54 g, 1.68 mol) of Compound 23 (12.0 g, 34.2 mmol) and potassium carbonate (4.72 g, 34.2 mmol) was stirred under argon atmosphere at room temperature for 4 hours. The liquid mixture was subjected to filtration, and then the filtrate was concentrated to obtain a red oily compound (8 g). The compound was subjected to short column chromatography (eluent: ethyl acetate) to obtain the target Compound 24 (yield amount: 5.9 g, 19.1 mmol, yield: 55%).

$^1$H NMR (CDCl$_3$, 400 MHz): δ4.73 (q, J=5.2 Hz, 2H), 4.17 (dd, J=12.8 and 1.2 Hz, 4H), 3.88-3.77 (m, 6H), 3.64

(dd, J=9.2 and 6.4 Hz, 2H), 3.25 (t, J=1.4 Hz, 2H), 3.22-3.13 (m, 1H), 2.10 (d, J=9.6 Hz, 1H), 1.33 (d, J=5.2 Hz, 6H)

$^{13}$C NMR (CDCl$_3$, 500 MHz): δ99.42 (CH×2), 77.36 (CH×2), 70.24 (CH$_2$×2), 68.96 (CH$_2$×2), 68.57 (CH$_2$×2), 39.72 (CH), 21.39 (CH$_3$×2)

(4) Deprotection

An aqueous solution (1.1 mL) of Compound 24 (172 mg, 0.55 mmol) and ion-exchange resin ("Amberlyst®" manufactured by Rohm and Haas) (6 mg) was stirred under argon atmosphere at 100° C. for 4 hours. After the obtained mixture was filtered, 2-propanol was added thereto and the mixture was concentrated to obtain Compound 25 as a yellow oil (yield amount: 139 mg, 0.54 mmol, yield: 99%). The obtained Compound 25 can be used as the hydrophilic metal surface treatment agent by binding a long chain alkyl compound through a disulfide bond or a thioester bond.

FT-IR (neat): 3370, 2932, 2878, 1652, 1465, 1407, 1347, 1120, 1050, 974, 904, 851 cm$^{-1}$ $^1$H NMR (CD$_3$OD, 500 MHz): δ3.88-3.87 (m, 4H, CHCH$_2$O), 3.67-3.55 (m, 8H, CHCH$_2$O) 3.44 (quint, J=5 Hz, 2H, OCH (CH$_2$)$_2$), 3.23 (quint, J=6 Hz, 1H, SCH (CH$_2$)$_2$)

$^{13}$C NMR (CD$_3$OD, 125 MHz): δ83.0 (CH×2, CHCH$_2$O) 70.5 (CH$_2$×2, CHCH$_2$O), 62.65 (CH$_2$×2, CHCH$_2$O), 62.58 (CH$_2$×2, CHCH$_2$O) 40.8 (CH, SCHCH$_2$)

HRMS (ESI-TOF) m/z calcd for C$_9$H$_{20}$O$_6$SNa [M+Na]$^+$ 279.0878 found 279.0882.

Example 5: Production of BGL Thiol

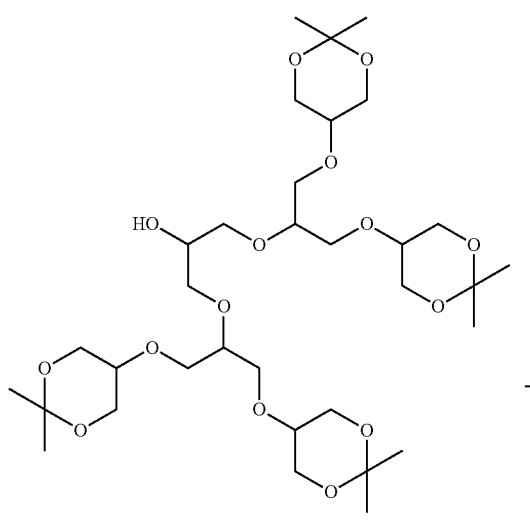

26

27 → 28 → 29 →
TsO—  AcS—  HS—

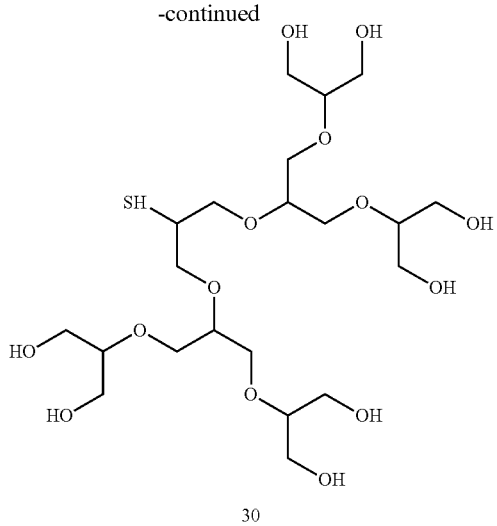

30

To a pyridine solution (5.0 mL) of Compound 26 (696.83 mg, 1.0 mmol) (NEMOTO Hisao et al., Synlett, 2007, 2091-2095), 4-toluenesulfonyl chloride (381.28 mg, 2.0 mmol) was added at 0° C. The mixture was stirred at 0° C. for 30 minutes and then at room temperature for 15 hours. The obtained mixture was poured to 5% KHSO$_4$ aqueous solution (80 mL), and extraction was repeated three times using ethyl acetate (100 mL). The collected extract was washed with saturated sodium hydrogencarbonate aqueous solution (50 mL) and saturated sodium chloride aqueous solution (50 mL), dried using anhydrous sodium sulfate and concentrated under reduced pressure. The obtained residue was directly used to the next reaction.

Potassium thioacetate (15.94 g, 139.57 mmol) was added to an acetonitrile solution (20 mL) of the above residue (theoretically 1.0 mmol), and the mixture was stirred at 80° C. for 15 hours. The obtained suspension was filtered, and the residue was washed using ethyl acetate. The filtrate and the wash fluid were combined and concentrated, and an oily residue was obtained using a short column (eluent: ethyl acetate). The residue was not further purified and used for the next reaction.

Potassium carbonate (138.21 mg, 1.0 mmol) was added to a methanol solution (30 mL) of the above residue (theoretically 1.0 mmol), and the obtained suspension was stirred at room temperature for 4 hours. The solid component in the obtained suspension was removed by filtration, and the filtrate was concentrated under reduced pressure. The residue was subjected to silica gel column chromatography (eluent: hexane/ethyl acetate=3/1) to obtain Compound 29 (yield amount: 452.35 mg, 0.60 mmol, yield: 60%).

Ion-exchange resin ("Amberlyst® 15" manufactured by Rohm and Haas) (50 mg) was added to a methanol solution (30 mL) of Compound 29, and the mixture was stirred at room temperature for 20 hours. The obtained suspension was filtered, and the filtrate was concentrated to obtain the target Compound 30 (yield amount: 314.99 mg, 0.57 mmol, yield: 95%). The obtained Compound 30 can be used as the hydrophilic metal surface treatment agent by binding to a long chain alkyl compound through a disulfide bond or a thioester bond.

Example 6: Water-Solubility Test

The hydrophilic metal surface treatment agent (Compound 21) (MW 608.86, 0.32 g) produced in Example 3 was added to ultrapure water (50.09 g), and the mixture was stirred after the water temperature was heated to 60° C. A particle aggregate of the hydrophilic metal surface treatment agent particle was formed in the early stage of the stirring, but the particle aggregate gradually became decomposed and dissolved as time advanced, and there was no visible undissolved residue after 3 hours.

With respect to even the hydrophilic metal surface treatment agent having an octadecyl group, i.e. n-$C_{18}H_{37}$, as a long chain hydrocarbon group, an aqueous solution having a concentration of 10.32 mM could be prepared.

Example 7: Measurement of Reflectivity Ratio

In the case of the conventional metal surface treatment agent containing the heterocyclic compound described in Patent document 3 and patent document 4 as the main component, a reflectivity ratio of a light on a metal surface is decreased by the surface treatment, since the main component absorbs the light having the specific wavelength.

On the one hand, a reflectivity ratio of the metal surface treated by the hydrophilic metal surface treatment agent having a hydrocarbon as a main component according to the present invention was measured.

(1) Preparation of Metal Surface Treatment Agent

As demonstrated in Example 6, the hydrophilic metal surface treatment agent of the present invention can be dissolved in water in a concentration of about 10 mM, even when an additive such as a surfactant and a solubilizing agent are not added. An aqueous solution, however, was prepared by adding an alkaline agent to the hydrophilic metal surface treatment agent aqueous solution in order to effectively bind the hydrophobic part in the hydrophilic metal surface treatment agent molecule on a metal surface.

(1-1) Metal Surface Treatment Agent Containing Alkaline Agent and Non-Ionic Surfactant A mixture of triethanolamine (10.0 g), polyoxyethylene-laurylamine (40.0 g) and ultrapure water (48.0 g) was heated at 60° C. and stirred to be a homogenous and viscous aqueous solution. The hydrophilic metal surface treatment agent (Compound 21) (2.0 g) produced in Example 3 was added to the aqueous solution, and the mixture was stirred for dissolution. The obtained aqueous solution (1.0 g) was added to ultrapure water (99.0 g) to be diluted 100 times to obtain a metal surface treatment agent.

(1-2) Metal Surface Treatment Agent Containing Alkaline Agent and Non-Ionic Surfactant Potassium carbonate (1.38 g) and polyoxyethylenelaurylamine (2.50 g) were dissolved in ultrapure water (95.48 g) with warming at 60° C. and stirring. The hydrophilic metal surface treatment agent (Compound 21) (0.64 g) produced in Example 3 was added to the obtained homogenous aqueous solution and dissolved by stirring the mixture at 60° C. The obtained aqueous solution (1.0 g) was added to ultrapure water (99.0 g) to be diluted 100 times to obtain a metal surface treatment agent.

(1-3) Metal Surface Treatment Agent Containing Alkaline Agent and Non-Ionic Surfactant Potassium hydrogencarbonate (1.00 g) and polyoxyethylenelaurylamine (2.50 g) were dissolved in ultrapure water (95.86 g) with warming at 60° C. and stirring. The hydrophilic metal surface treatment agent (Compound 21) (0.64 g) produced in Example 3 was added to the obtained homogenous aqueous solution and dissolved by stirring the mixture at 60° C. The obtained aqueous solution (1.0 g) was added to ultrapure water (99.0 g) to be diluted 100 times to obtain a metal surface treatment agent.

(2) Treatment of Metal Sample Surface

A plain plate of thickness 200 μm×2 cm×3 cm with Au coat or Ag coat was immersed in each metal surface treatment agent (100 mL) warmed to 55° C. for 3 hours. Then, the metal sample was taken out from the metal surface treatment agent, washed with ultrapure water, and then dried using a dryer.

(3) Measurement of Reflectivity Ratio

The surface of the metal sample was observed under magnification at 10 to 50 times using a digital microscope ("VHX-6000" manufactured by KEYENCE) before and after the above treatment. As a result, a noticeable change in appearance was not observed.

In addition, a reflectivity ratio of visible light (wavelength: 380 to 780 nm) on the surface of the metal sample before and after the above treatment was measured using an ultraviolet-visible spectrophotometer ("U-3900" manufactured by Hitachi High-Tech Science). As a result, reflectivity ratio curves of any of the treated metal samples of the above (1-1) to (1-3) were nearly the same as reflectivity ratio curves of untreated metal samples.

Example 8: Water Repellency Test

An example of the cause for the corrosion of a metal includes the moisture adsorbed on the metal surface. A contact angle, therefore, was measured in order to evaluate the change of a water repellency of a metal surface due to the hydrophilic metal surface treatment agent of the present invention.

A plain plate of thickness 200 μm×2 cm×3 cm with Au coat or Ag coat was immersed in each metal surface treatment agent (100 mL) warmed to 55° C. for 10 seconds, 30 seconds or 6 hours. Then, the metal sample was taken out from the metal surface treatment agent, washed with ultrapure water, and then dried using a dryer.

On the surface of each treated metal sample or untreated metal sample, 1 μL of ultrapure water was added dropwise. The sample was left to stand for 10 seconds. Then, a contact angle of the water droplet on the surface was measured using a contact angle meter ("Drop Master 300" manufactured by Kyowa Interface Science). The result is shown in Table 1.

TABLE 1

|  | Untreated | 10 s Treatment Treatment agent 1-1 | 30 s Treatment Treatment agent 1-3 | 6 h Treatment Treatment agent 1-1 | 6 h Treatment Treatment agent 1-3 |
|---|---|---|---|---|---|
| Au coated plate | 67.1° | 98.6° | 103.5° | 108.7° | 109.4° |
| Ag coated plate | 94.7° | 105.9° | 108.4° | 109.1° | 107.4° |

It was confirmed as the result shown in Table 1 that a contact angle on the surface of both of an Au coated plate and an Ag coated plate is increased and a water repellency is improved by the treatment with the hydrophilic metal surface treatment agent of the present invention in comparison with an untreated plate.

Example 9: Corrosion Resistance Test 1

Potassium sulfide test was carried out to evaluate an effect to improve a corrosion resistance by the hydrophilic metal surface treatment agent of the present invention.

Specifically, a plain plate of thickness 200 μm×2 cm×3 cm with Ag coat was immersed in each metal surface treatment agent (100 mL) warmed to 55° C. for 3 hours. Then, the metal sample was taken out from the metal surface treatment agent, washed with ultrapure water, and then dried using a dryer.

The Ag coated plate of which surface was treated was immersed in 5% potassium sulfide aqueous solution for 2 minutes or 15 minutes. Then, the metal sample was taken out from the potassium sulfide aqueous solution, washed with ultrapure water, and then dried using a dryer. In addition, untreated Ag coated plate was similarly treated for comparison. The result is shown in FIG. 1.

As the result shown in FIG. 1, a part which was immersed in a potassium sulfide aqueous solution for 2 minutes in untreated Ag coated plate became discolored to brown-magenta, and the color was further changed by the treatment for 15 minutes. On the one hand, a discolorment was not observed in the Ag coated plate treated by using the hydrophilic metal surface treatment agent of the present invention, and a glossy appearance specific to Ag was maintained. Thus, the hydrophilic metal surface treatment agent of the present invention can protect a metal from an impact of potassium sulfide.

Example 10: Corrosion Resistance Test 2

Hydrogen sulfide test was carried out to evaluate an effect to improve a corrosion resistance by the hydrophilic metal surface treatment agent of the present invention.

Specifically, a plain plate of thickness 200 μm×2 cm×3 cm with Ag coat was immersed in each metal surface treatment agent (100 mL) warmed to 55° C. for 3 hours. Then, the metal sample was taken out from the metal surface treatment agent, washed with ultrapure water, and then dried using a dryer.

The above treated metal sample and an untreated metal sample were exposed to a hydrogen sulfide gas using a constant flow-type gas corrosion tester ("GH-180" manufactured by Yamasaki Seiki Kenkyusho, Inc.) for 24 hour or 48 hours. A concentration of a hydrogen sulfide gas in the test chamber of the tester was adjusted to 3 ppm, a chamber temperature was adjusted to 40° C., and a chamber humidity was adjusted to 80% RH. In addition, an untreated Ag coated plate was similarly treated for comparison. The result is shown in FIG. 2.

As the result shown in FIG. 2, the untreated Ag coated plate became discolored to ultramarine-blue after the exposure to a hydrogen sulfide gas for 24 to 48 hours.

On the one hand, the effect of the hydrophilic metal surface treatment agent according to the present invention to improve a corrosion resistance could be confirmed, since the color specific to Ag coating of the Ag coated plate treated by the hydrophilic metal surface treatment agent of the present invention was maintained even after the plate was exposed to a hydrogen sulfide gas for 24 hours or 48 hours.

Example 11: Corrosion Resistance Test 3

A sodium chloride aqueous solution spray test was carried out to evaluate an effect to improve a corrosion resistance by the hydrophilic metal surface treatment agent of the present invention.

Specifically, a plain plate of thickness 200 μm×2 cm×3 cm with Au coat or Ag coat was immersed in each metal surface treatment agent (100 mL) warmed to 55° C. for 6 hours. Then, the metal sample was taken out from the metal surface treatment agent, washed with ultrapure water, and then dried using a dryer.

A sodium chloride aqueous solution was sprayed on the above treated metal sample and an untreated metal sample using a salt spray test instrument ("STP-90V-2" manufactured by Suga Test Instruments). A concentration of the sodium chloride aqueous solution was adjusted to 5%, a temperature of the spray chamber was adjusted to 35° C., an amount of the sprayed sodium chloride aqueous solution was adjusted to 1.5±0.5 mL/80 cm$^2$/hour, a time to spray the sodium chloride aqueous solution on the Au coated plate was adjusted to 16 hours, and a time to spray the sodium chloride aqueous solution on the Ag coated plate was adjusted to 48 hours or 72 hours. In addition, an untreated Au coated plate and an untreated Ag coated plate were similarly treated for comparison. The result of the Au coated plate is shown in FIG. 3, and the result of the Ag coated plate is shown in FIG. 4.

As the results shown in FIG. 3 and FIG. 4, white corrosion was generated on the both surfaces of the untreated Au coated plate and the untreated Ag coated plate.

On the one hand, a corrosion due to a sodium chloride aqueous solution was not generated at all on the Au coated plate and the Ag coated plate treated by the hydrophilic metal surface treatment agent of the present invention, and it was observed that a good appearance was maintained.

Example 12: Evaluation of Sliding Property

A friction coefficient of a metal surface was measured to evaluate an effect to improve a sliding property by the hydrophilic metal surface treatment agent of the present invention.

Specifically, a plain plate of thickness 200 μm×2 cm×3 cm with Au coat was immersed in each metal surface treatment agent (100 mL) warmed to 55° C. for 6 hours. Then, the metal sample was taken out from the metal surface treatment agent, washed with ultrapure water, and then dried using a dryer.

A measuring probe was slid on the metal sample surface using a precise sliding test apparatus ("CRS-G2050-CHD-A" manufactured by Yamasaki Seiki) to measure a friction coefficient. With respect to the test condition, a load was 50 gf, a slide speed was 0.33 mm/sec, a slide distance was 0.5 mm, a measurement current was 1 mA, a probe diameter was 1.5 mm, and measurement number was 30 times. In addition, an untreated Au coated plate was similarly subjected to the measurement for comparison. The result is shown in Table 2.

TABLE 2

|  | Initial friction coefficient | Friction coefficient after 30 timesslides |
|---|---|---|
| Untreated metal sample | 0.39 | 0.58 |
| Treated metal sample | 0.15 | 0.49 |

As the result shown in Table 2, an initial friction coefficient of the untreated Au coated plate was 0.39 and a friction coefficient after 30 times slide was increased to 0.58. On the one hand, in the case of the Au coated plate treated by the hydrophilic metal surface treatment agent of the present invention, an initial friction coefficient was 0.15 and a friction coefficient after 30 times slide was 0.49. Thus, in the case of the Au coated plate treated by the hydrophilic metal surface treatment agent of the present invention, it was confirmed that an initial friction coefficient is reduced and a friction coefficient after a slide is lower than that of an untreated Au coat.

Example 13: Evaluation of Electrochemical Migration Resistance Property

Electrochemical migration means a phenomenon of a short-circuit between electrodes in an electrical circuit by deteriorating an insulation property between the electrodes electrically, chemically or due to heat or by dissolving or reducing an electrode metal as an ion. ECM test was carried out and an insulation resistance value under a load of applied voltage was measured to evaluate an electrochemical migration (ECM) resistance property of an Ag coated comb-shaped electrode pattern substrate of which surface was treated by the hydrophilic metal surface treatment agent of the present invention.

Specifically, a plain plate of thickness 200 μm×2 cm×3 cm with Ag coat was immersed in each metal surface treatment agent (100 mL) warmed to 55° C. for 6 hours. Then, the metal sample was taken out from the metal surface treatment agent, washed with ultrapure water, and then dried using a dryer. Comb-shaped copper electrodes having a width of 100 μm and a thickness of 18 μm were formed at 100 μm intervals, i.e. L/S=100 μm, on an Ag coated plate. The comb-shaped copper electrodes were coated with Ni in a thickness of 3.0 μm as a base and coated with Au in a thickness of 0.15 μm as a surface layer.

An applied voltage was loaded on an evaluation substrate using an ion migration tester ("ECM-100" manufactured by J-RAS) and a thermo-hygrostat bath manufactured by Nagano Science, and a change of an insulation resistance value during the application was measured. With respect to the test condition, the applied DC voltage was 20 V, the chamber temperature was 85° C., the chamber humidity was 85% RH, and the energizing time was 120 hours. An Ag coated comb-shaped electrode pattern substrate of which outermost surface was Ag coating treated by the hydrophilic metal surface treatment agent of the present invention was used as a substrate for evaluation. An untreated Ag coated plate was also subjected to the similar measurement for comparison.

As a result, a short circuit (ECM) occurred during the energizing period of 120 hours and the insulation resistance value was decreased to $1.0 \times 10^6 \Omega$ or less in the untreated substrate. On the one hand, it was confirmed in the case of the Ag coated substrate of which surface was treated by the hydrophilic metal surface treatment agent of the present invention that the occurrence of ECM was suppressed, since the insulation resistance value was maintained at $1.0 \times 10^{10} \Omega$ or more as the early stage insulation resistance value during the energizing period.

The invention claimed is:

1. A hydrophilic metal surface treatment agent comprising a branched glycerol derivative represented by the following formula (I) as an active ingredient:

$$R^1-S-X-Y\left[-O-\left\langle\begin{array}{l}-OH\\-OH\end{array}\right.\right]_n \quad (I)$$

wherein
   $R^1$ is a hydrocarbon group having a carbon number of 10 or more and 30 or less,
   X is S or a carbonyl group,
   Y is an n+1 valent linker group,
   n is an integer of 1 or more and 5 or less.

2. The hydrophilic metal surface treatment agent according to claim 1, comprising water as a solvent.

3. The hydrophilic metal surface treatment agent according to claim 2, wherein a concentration of the branched glycerol derivative represented by the formula (I) is 0.005 mM or more and 5 mM or less.

4. The hydrophilic metal surface treatment agent according to claim 2, wherein a concentration of the branched glycerol derivative represented by the formula (I) is 0.001 mass % or more and 5 mass % or less.

5. The hydrophilic metal surface treatment agent according to claim 1, further comprising an alkaline agent.

6. The hydrophilic metal surface treatment agent according to claim 1, further comprising a surfactant.

7. A method for treating a surface of a metal, comprising the step of treating the surface of the metal by using the hydrophilic metal surface treatment agent according to claim 1.

8. The method according to claim 7, wherein the surface of the metal is treated by immersing the metal in the hydrophilic metal surface treatment agent in liquid form, applying the hydrophilic metal surface treatment agent to the surface of the metal, or spraying the hydrophilic metal surface treatment agent on the surface of the metal.

9. The method according to claim 7, wherein the metal is gold, silver, platinum, palladium, tin, aluminum, nickel, iron, copper, zinc or an alloy thereof.

10. A protected branched glycerol derivative represented by the following formula (II):

$$\text{HO}-\left\langle\begin{array}{l}-O-\left\langle\begin{array}{l}O\\O\end{array}\right\rangle R^2\\-O-\left\langle\begin{array}{l}O\\O\end{array}\right\rangle R^2\end{array}\right. \quad (II)$$

wherein $R^2$ is a $C_{1-6}$ alkyl group.

11. A method for producing a protected branched glycerol derivative represented by the following formula (II):

$$\text{HO}-\left\langle\begin{array}{l}-O-\left\langle\begin{array}{l}O\\O\end{array}\right\rangle R^2\\-O-\left\langle\begin{array}{l}O\\O\end{array}\right\rangle R^2\end{array}\right. \quad (II)$$

wherein $R^2$ is a $C_{1-6}$ alkyl group, comprising the steps of:

reacting glycerin with an aldehyde compound $R^2$—CHO to obtain a mixture comprising the compounds represented by the following formulae (III-1) to (III-4):

(III-1)
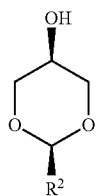

(III-2)
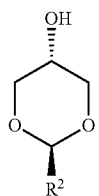

(III-3)
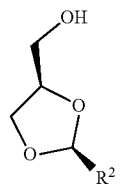

(III-4)
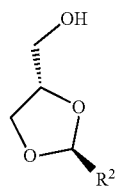

wherein $R^2$ has the same meaning as the above, purifying the compound represented by the formula (III-1) from the mixture by distillation, and reacting the compound represented by the formula (III-1) with an epihalohydrin to obtain the protected branched glycerol derivative represented by the formula (II).

12. The hydrophilic metal surface treatment agent according to claim 4, further comprising a surfactant.

* * * * *